US012810965B2

(12) United States Patent
Mellen et al.

(10) Patent No.: US 12,810,965 B2
(45) **Date of Patent: *Nov. 24, 2026**

(54) SYSTEMS AND METHODS FOR VISUALIZATION OF SINGLE-CELL RESOLUTION CHARACTERISTICS

(71) Applicant: 10X Genomics, Inc., Pleasanton, CA (US)

(72) Inventors: Jeffrey Mellen, Martinez, CA (US); Kevin J. Wu, San Francisco, CA (US); Vijay Kumar Sreenivasa Gopalan, Santa Clara, CA (US); Nicolaus Lance Hepler, San Diego, CA (US); Jasper Staab, Honolulu, HI (US)

(73) Assignee: 10X Genomics, Inc., Pleasanton, CA (US)

( * ) Notice: Subject to any disclaimer, the term of this patent is extended or adjusted under 35 U.S.C. 154(b) by 198 days.

This patent is subject to a terminal disclaimer.

(21) Appl. No.: 18/752,522

(22) Filed: Jun. 24, 2024

(65) Prior Publication Data

US 2024/0347137 A1 Oct. 17, 2024

Related U.S. Application Data

(63) Continuation of application No. 18/165,133, filed on Feb. 6, 2023, now Pat. No. 12,062,418, which is a
(Continued)

(51) Int. Cl.

| | |
|---|---|
| ***G16B 45/00*** | (2019.01) |
| ***C12Q 1/68*** | (2018.01) |
| ***G16B 20/40*** | (2019.01) |

(52) U.S. Cl.

CPC ............... *G16B 45/00* (2019.02); *C12Q 1/68* (2013.01); *G16B 20/40* (2019.02)

(58) Field of Classification Search

USPC ........................................................... 702/19

See application file for complete search history.

(56) References Cited

U.S. PATENT DOCUMENTS

| | | | | |
|---|---|---|---|---|
| 10,095,831 | B2 * | 10/2018 | Duenwald | G16B 25/00 |
| 2013/0060775 | A1 | 3/2013 | Qiu et al. | |

(Continued)

FOREIGN PATENT DOCUMENTS

WO WO 2018089378 A1 5/2018

OTHER PUBLICATIONS

Chimenti, "10X Genomics Loupe Single Cell Browser Explained in 7 minutes", Youtube, Apr. 16, 2018, page 1 pp. Retrieved from the Internet: URL: https://www.youtube.com/watch?v=VAbMRkeAJYY.

(Continued)

*Primary Examiner* — Pierre E Elisca

(57) ABSTRACT

A visualization system comprising processing cores, memory, and a display performs a visualization method by obtaining a block of data. The data represents a single-cell characteristic of cells in a plurality of cells across each bin in a plurality of bins. Each bin maps to a different portion of a reference genome. The cells are clustered based upon the single-cell characteristic across the plurality of bins, thereby forming a tree structure that includes a current root node, a plurality of intermediate nodes, and the plurality of cells. Th plurality of cells constitute terminal nodes in the tree structure and each respective intermediate node has a corresponding plurality of daughter nodes, each daughter node being an intermediate node or a cell. The single-cell characteristic is plotted for the current root node of the tree on the screen using the dataset, across all or the portion of the plurality of bins.

20 Claims, 23 Drawing Sheets

Related U.S. Application Data continuation of application No. 16/454,485, filed on Jun. 27, 2019, now Pat. No. 11,574,706.

(60) Provisional application No. 62/691,593, filed on Jun. 28, 2018.

(56) References Cited

U.S. PATENT DOCUMENTS

| | | | | |
|---|---|---|---|---|
| 2017/0220735 | A1* | 8/2017 | Duenwald .............. | G16B 20/20 |
| 2018/0010179 | A1 | 1/2018 | Hansen et al. | |
| 2018/0216162 | A1 | 8/2018 | Belhocine et al. | |
| 2019/0065676 | A1* | 2/2019 | Duenwald ............... | G16Z 99/00 |

OTHER PUBLICATIONS

Garvin et al., "Interactive analysis and assessment of single-cell copy-number variations", Nature Methods, Nov. 1, 2015, vol. 12, No. 11, pp. 1058-1050. [Published online Sep. 7, 2015].

Garvin et al., "Supplementary Text ad Figures. Interactive analysis and assessment of single-cell copy-number variations", Nature Methods, Sep. 7, 2015, vol. 12, No. 11, pp. 1058-1050.

Hillt et al., "CyteGuide: Visual Guidance for Hierarchical Single-Cell Analysis", IEEE Transations on Visualization and Computer Graphics, IDDD Service Center, Los Alamos, CA, Jan. 1, 2018, vol. 24, No. 1, pp. 739-748.

Lee et al., "Third-generation sequencing and the future of genomics", BioRxiv, posted online Apr. 13, 2016,; doi:http://dx.doi.org/10.1101/048603.

Navin et al., "Tumour evolution inferred by single-cell sequencing", Nature, Mar. 13, 2011, vol. 472, No. 7341, pp. 90-94.

Navin et al., "Supplementary Information. Tumour evolution inferred by single-cell sequencing", Nature, Mar. 13, 2011, vol. 472, No. 7341, pp. 90-94.

Pal et al., "Intramolecular Cooperativity in a Protein Binding Site Assessed by Combinatorial Shotgun Scanning Mutagenesis", Journal of Molecular Biology, (2005) 347, pp. 489-494.

Qiu et al., "Extracting a cellular hierarchy from high-dimensional cytometry data with SPADE", Nature Biotechnology, Oct. 1, 2011, vol. 29, No. 10.

Zheng et al., "Haplotyping germline and cancer genomes using high-throughput linked-read sequencing", Nature Biotechnology, Mar. 2016, 34(3): 303-311. doi:1038/nbt.3432.

* cited by examiner

Copy number block
132

| | Bin 1 | Bin 2 | Bin 3 | Bin 4 | Bin 5 | ••• | Bin N |
|---|---|---|---|---|---|---|---|
| Node 1 | C. Number 1-1 | C. Number 2-1 | C. Number 3-1 | C. Number 4-1 | C. Number 5-1 | ••• | C. Number N-1 |
| Node 2 | C. Number 1-2 | C. Number 2-2 | C. Number 3-2 | C. Number 4-2 | C. Number 5-2 | ••• | C. Number N-2 |
| Node 3 | C. Number 1-3 | C. Number 2-3 | C. Number 3-3 | C. Number 4-3 | C. Number 5-3 | ••• | C. Number N-3 |
| Node 4 | C. Number 1-4 | C. Number 2-4 | C. Number 3-4 | C. Number 4-4 | C. Number 5-4 | ••• | C. Number N-4 |
| Node 5 | C. Number 1-5 | C. Number 2-5 | C. Number 3-5 | C. Number 4-5 | C. Number 5-5 | ••• | C. Number N-5 |
| Node 6 | C. Number 1-6 | C. Number 2-6 | C. Number 3-6 | C. Number 4-6 | C. Number 5-6 | ••• | C. Number N-6 |
| Node 7 | C. Number 1-7 | C. Number 2-7 | C. Number 3-7 | C. Number 4-7 | C. Number 5-7 | ••• | C. Number N-7 |
| ⋮ | ⋮ | ⋮ | ⋮ | ⋮ | ⋮ | ⋮ | ⋮ |
| Node T | C. Number 1-T | C. Number 2-T | C. Number 3-T | C. Number 4-T | C. Number 5-T | ••• | C. Number N-T |

Figure 1C

Heterogeneity block
136

| | Bin 1 | Bin 2 | Bin 3 | Bin 4 | Bin 5 | ••• | Bin N |
|---|---|---|---|---|---|---|---|
| Node 1 | Heter 1-1 | Heter 2-1 | Heter 3-1 | Heter 4-1 | Heter 5-1 | ••• | Heter N-1 |
| Node 2 | Heter 1-2 | Heter 2-2 | Heter 3-2 | Heter 4-2 | Heter 5-2 | ••• | Heter N-2 |
| Node 3 | Heter 1-3 | Heter 2-3 | Heter 3-3 | Heter 4-3 | Heter 5-3 | ••• | Heter N-3 |
| Node 4 | Heter 1-4 | Heter 2-4 | Heter 3-4 | Heter 4-4 | Heter 5-4 | ••• | Heter N-4 |
| Node 5 | Heter 1-5 | Heter 2-5 | Heter 3-5 | Heter 4-5 | Heter 5-5 | ••• | Heter N-5 |
| Node 6 | Heter 1-6 | Heter 2-6 | Heter 3-6 | Heter 4-6 | Heter 5-6 | ••• | Heter N-6 |
| Node 7 | Heter 1-7 | Heter 2-7 | Heter 3-7 | Heter 4-7 | Heter 5-7 | ••• | Heter N-7 |
| ⋮ | ⋮ | ⋮ | ⋮ | ⋮ | ⋮ | ⋮ | ⋮ |
| Node T | Heter 1-T | Heter 2-T | Heter 3-T | Heter 4-T | Heter 5-T | ••• | Heter N-T |

Figure 1D

Confidence block 140

| | Bin 1 | Bin 2 | Bin 3 | Bin 4 | Bin 5 | ... | Bin N |
|---|---|---|---|---|---|---|---|
| Node 1 | Conf 1-1 | Conf 2-1 | Conf 3-1 | Conf 4-1 | Conf 5-1 | ... | Conf N-1 |
| Node 2 | Conf 1-2 | Conf 2-2 | Conf 3-2 | Conf 4-2 | Conf 5-2 | ... | Conf N-2 |
| Node 3 | Conf 1-3 | Conf 2-3 | Conf 3-3 | Conf 4-3 | Conf 5-3 | ... | Conf N-3 |
| Node 4 | Conf 1-4 | Conf 2-4 | Conf 3-4 | Conf 4-4 | Conf 5-4 | ... | Conf N-4 |
| Node 5 | Conf 1-5 | Conf 2-5 | Conf 3-5 | Conf 4-5 | Conf 5-5 | ... | Conf N-5 |
| Node 6 | Conf 1-6 | Conf 2-6 | Conf 3-6 | Conf 4-6 | Conf 5-6 | ... | Conf N-6 |
| Node 7 | Conf 1-7 | Conf 2-7 | Conf 3-7 | Conf 4-7 | Conf 5-7 | ... | Conf N-7 |
| ⋮ | ⋮ | ⋮ | ⋮ | ⋮ | ⋮ | ⋮ | ⋮ |
| Node T | Conf 1-T | Conf 2-T | Conf 3-T | Conf 4-T | Conf 5-T | ... | Conf N-T |

Figure 1E

Quantized read depth data block 144

| | Bin 1 | Bin 2 | Bin 3 | Bin 4 | Bin 5 | ••• | Bin N |
|---|---|---|---|---|---|---|---|
| Node 1 | Depth 1-1 | Depth 2-1 | Depth 3-1 | Depth 4-1 | Depth 5-1 | ••• | Depth N-1 |
| Node 2 | Depth 1-2 | Depth 2-2 | Depth 3-2 | Depth 4-2 | Depth 5-2 | ••• | Depth N-2 |
| Node 3 | Depth 1-3 | Depth 2-3 | Depth 3-3 | Depth 4-3 | Depth 5-3 | ••• | Depth N-3 |
| Node 4 | Depth 1-4 | Depth 2-4 | Depth 3-4 | Depth 4-4 | Depth 5-4 | ••• | Depth N-4 |
| Node 5 | Depth 1-5 | Depth 2-5 | Depth 3-5 | Depth 4-5 | Depth 5-5 | ••• | Depth N-5 |
| Node 6 | Depth 1-6 | Depth 2-6 | Depth 3-6 | Depth 4-6 | Depth 5-6 | ••• | Depth N-6 |
| Node 7 | Depth 1-7 | Depth 2-7 | Depth 3-7 | Depth 4-7 | Depth 5-7 | ••• | Depth N-7 |
| ⋮ | ⋮ | ⋮ | ⋮ | ⋮ | ⋮ | ⋮ | ⋮ |
| Node T | Depth 1-T | Depth 2-T | Depth 3-T | Depth 4-T | Depth 5-T | ••• | Depth N-T |

Figure 1F

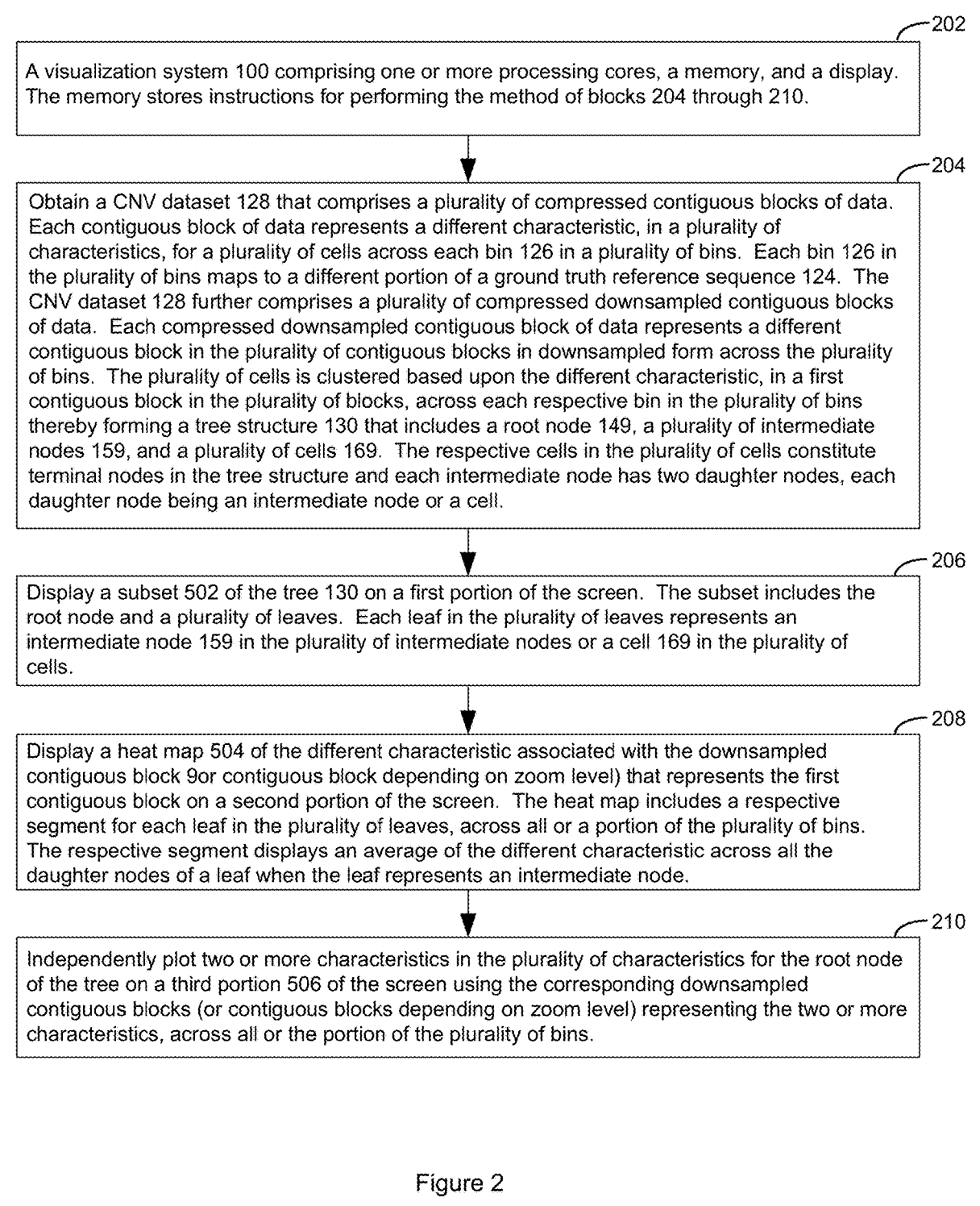

202

A visualization system 100 comprising one or more processing cores, a memory, and a display. The memory stores instructions for performing the method of blocks 204 through 210.

204

Obtain a CNV dataset 128 that comprises a plurality of compressed contiguous blocks of data. Each contiguous block of data represents a different characteristic, in a plurality of characteristics, for a plurality of cells across each bin 126 in a plurality of bins. Each bin 126 in the plurality of bins maps to a different portion of a ground truth reference sequence 124. The CNV dataset 128 further comprises a plurality of compressed downsampled contiguous blocks of data. Each compressed downsampled contiguous block of data represents a different contiguous block in the plurality of contiguous blocks in downsampled form across the plurality of bins. The plurality of cells is clustered based upon the different characteristic, in a first contiguous block in the plurality of blocks, across each respective bin in the plurality of bins thereby forming a tree structure 130 that includes a root node 149, a plurality of intermediate nodes 159, and a plurality of cells 169. The respective cells in the plurality of cells constitute terminal nodes in the tree structure and each intermediate node has two daughter nodes, each daughter node being an intermediate node or a cell.

206

Display a subset 502 of the tree 130 on a first portion of the screen. The subset includes the root node and a plurality of leaves. Each leaf in the plurality of leaves represents an intermediate node 159 in the plurality of intermediate nodes or a cell 169 in the plurality of cells.

208

Display a heat map 504 of the different characteristic associated with the downsampled contiguous block 9or contiguous block depending on zoom level) that represents the first contiguous block on a second portion of the screen. The heat map includes a respective segment for each leaf in the plurality of leaves, across all or a portion of the plurality of bins. The respective segment displays an average of the different characteristic across all the daughter nodes of a leaf when the leaf represents an intermediate node.

210

Independently plot two or more characteristics in the plurality of characteristics for the root node of the tree on a third portion 506 of the screen using the corresponding downsampled contiguous blocks (or contiguous blocks depending on zoom level) representing the two or more characteristics, across all or the portion of the plurality of bins.

Figure 2

SYSTEMS AND METHODS FOR VISUALIZATION OF SINGLE-CELL RESOLUTION CHARACTERISTICS

CROSS REFERENCE TO RELATED APPLICATION

This application is a continuation of U.S. patent application Ser. No. 18/165,133 entitled "Systems and Methods for Visualizing of Single-Cell Resolution Characteristics," filed Feb. 6, 2023, which is a continuation of U.S. patent application Ser. No. 16/454,485 entitled "Systems and Methods for Visualizing of Single-Cell Resolution Characteristics," filed Jun. 27, 2019 (now U.S. Pat. No. 11,574,706) entitled "Systems and Methods for Visualizing of Single-Cell Resolution Characteristics," which claims priority to U.S. Provisional Patent Application No. 62/691,593, entitled "Systems and Methods for Visualizing a Pattern in a Dataset," filed Jun. 28, 2018, each of which is hereby incorporated by reference.

TECHNICAL FIELD

This specification describes technologies relating to visualizing patterns in datasets.

BACKGROUND

Advances in single cell nucleic acid sequencing have given rise to rich datasets for cell populations. Such sequencing techniques provide data for cell populations that can be used to determine genomic heterogeneity, including genomic copy number variation, as well as for mapping clonal evolution (e.g., evaluation of the evolution of tumors). However, such sequencing datasets are complex and, consequently, tools are needed to allow for a scalable approach to analyzing such datasets in order to determine genomic heterogeneity such as copy number variation, map clonal evolution, and/or identification of somatic variation even in a single cell.

SUMMARY

Technical solutions (e.g., computing systems, methods, and non-transitory computer readable storage mediums) for addressing the above identified problems with discovery patterns in datasets are provided in the present disclosure.

The present disclosure provides a comprehensive, scalable approach to determine genomic heterogeneity and map clonal evolution by profiling hundreds to thousands of cells in a single sample. Single cell DNA sequencing data is aligned to a reference genome and copy number variation (CNV) is investigated on the scale of chromosomes down to 100,000 or fewer base pairs, allowing for the identification of somatic variation even in a single cell. The visualization tools allow identification and exploration of single cells and groups of cells defined by their mutual similarity. An interactive visualization tool is provided to browse groups by a tree structure, investigate groups of cells or individual cells by copy number or heterogeneity, and view copy number variation by genes.

The following presents a summary of the invention in order to provide a basic understanding of some of the aspects of the invention. This summary is not an extensive overview of the invention. It is not intended to identify key/critical elements of the invention or to delineate the scope of the invention. Its sole purpose is to present some of the concepts of the invention in a simplified form as a prelude to the more detailed description that is presented later.

One aspect of the present disclosure provides a visualization system. The visualization system comprises one or more processing cores, a memory, and a display. The memory collectively stores instructions for performing a method for visualizing a pattern using the memory and the display. The method comprises obtaining a dataset that, in turn, comprises a plurality of compressed contiguous blocks of data, where each contiguous block of data represents a different single-cell characteristic, in a plurality of single-cell characteristics, for each of a plurality of cells across each bin in a plurality of bins, and where each respective bin in the plurality of bins maps to a different portion of a reference genome (e.g., a reference human genome). The dataset further comprises a plurality of compressed downsampled contiguous blocks of data, each compressed downsampled contiguous block of data representing a different contiguous block in the plurality of contiguous blocks in downsampled form across the plurality of bins.

The plurality of cells is clustered based upon the different single-cell characteristic, in a first contiguous block in the plurality of blocks, across each respective bin in the plurality of bins thereby forming a tree structure that includes a root node, a plurality of intermediate nodes, and a plurality of cells. The cells in the plurality of cells constitute terminal nodes in the tree structure and each intermediate node has daughter nodes, each such daughter node being an intermediate node or a cell.

A subset of the tree is displayed on a first portion of the screen, where the subset includes the root node and a plurality of leaves. Each leaf in the plurality of leaves represents an intermediate node in the plurality of intermediate nodes or a cell in the plurality of cells.

A heat map of the different single-cell characteristic is displayed on a second portion of the screen. The heat map includes a respective segment for each leaf in the plurality of leaves, across all or a portion of the plurality of bins. The respective segment includes an average of the different single-cell characteristic across all the daughter nodes of a leaf when the leaf represents an intermediate node. Depending on zoom scale, the heat map uses values for the different single-cell characteristic either from the downsampled contiguous block that represents the different single-cell characteristic or directly from the contiguous block that represents the different single-cell characteristic. For instance, when sufficiently zoomed in, the heat map shows rectangles that represent a single bin at original bin resolution (e.g., 20 kb) using values for the different characteristic from the contiguous block. In other zoom instances, the heat map shows downsampled values for the different characteristic from the downsampled contiguous block that represents the different characteristic.

There is separately plotted two or more single-cell characteristics in the plurality of characteristics for the root node of the tree on a third portion of the screen using the corresponding contiguous blocks representing the two or more single-cell characteristics, across all or the portion of the plurality of bins. Depending on zoom scale, these plots use values for the different single-cell characteristic either from the downsampled contiguous blocks corresponding to the two or more single-cell characteristics or directly from the contiguous blocks corresponding to the two or more single-cell characteristics. For instance, when sufficiently zoomed in, the plots show individual datapoints per bin for the two or more single-cell characteristics from the contiguous blocks representing the two or more single-cell characteristics. In other zoom instances, the plots show values for the two or more characteristics from the downsampled contiguous block that represents the two or more characteristics.

In some embodiment, the plurality of cells is clustered on a computer system remote from the visualization system prior to obtaining the dataset.

In some embodiments, the single-cell characteristic in the plurality of characteristics comprises is copy number, heterogeneity, confidence, or read depth.

In some embodiments, the plurality of cells is obtained from a single human subject. In some embodiments, the plurality of cells comprises 1000 cells, 10,000 cells, or more than 10,000 cells.

In some embodiments, the method further comprises, responsive to a selection of an intermediate node in the plurality of nodes, providing a collective composition of the nodes in a portion of the tree structure that directly or indirectly descend from the intermediate node. In some such embodiments, the dataset comprises data from a plurality of gem wells and the collective composition includes a percentage of nodes in the portion of the tree structure that directly or indirectly descend from the intermediate node for each gem well in the plurality of gem wells.

In some embodiments, the plurality of cells is clustered by hierarchical clustering, agglomerative clustering using a nearest-neighbor algorithm, agglomerative clustering using a farthest-neighbor algorithm, agglomerative clustering using an average linkage algorithm, agglomerative clustering using a centroid algorithm, agglomerative clustering using a sum-of-squares algorithm, clustering by a Louvain modularity algorithm, k-means clustering, a fuzzy k-means clustering algorithm, or Jarvis-Patrick clustering.

In some embodiments, the corresponding plurality of daughter nodes for each respective intermediate node consists of two nodes.

In some embodiments, a single-cell characteristic in the plurality of single-cell characteristics is obtained by single cell sequencing of the plurality of cells. In some embodiments, each single-cell characteristic in the plurality of single-cell characteristics is obtained by single cell sequencing of the plurality of cells.

In some embodiments, the plurality of single-cell characteristics comprises three or more single-cell characteristics. In some embodiments, the corresponding plurality of daughter nodes for a respective intermediate node in the tree comprises two or more nodes.

Various embodiments of systems, methods and devices within the scope of the appended claims each have several aspects, no single one of which is solely responsible for the desirable attributes described herein. Without limiting the scope of the appended claims, some prominent features are described herein. After considering this discussion, and particularly after reading the section entitled "Detailed Description" one will understand how the features of various embodiments are used.

INCORPORATION BY REFERENCE

All publications, patents, and patent applications mentioned in this specification are herein incorporated by reference in their entireties to the same extent as if each individual publication, patent, or patent application was specifically and individually indicated to be incorporated by reference.

BRIEF DESCRIPTION OF THE DRAWINGS

The implementations disclosed herein are illustrated by way of example, and not by way of limitation, in the figures of the accompanying drawings. Like reference numerals refer to corresponding parts throughout the several views of the drawings.

FIGS. 1A, 1B, 1C, 1D, 1E, and 1F are an example block diagram illustrating a computing device and related data structures used by the computing device in accordance with some implementations.

FIG. 2 illustrates an example method in accordance with an embodiment of the present disclosure, in which optional steps are indicated by broken lines.

DETAILED DESCRIPTION

Figure 1A:
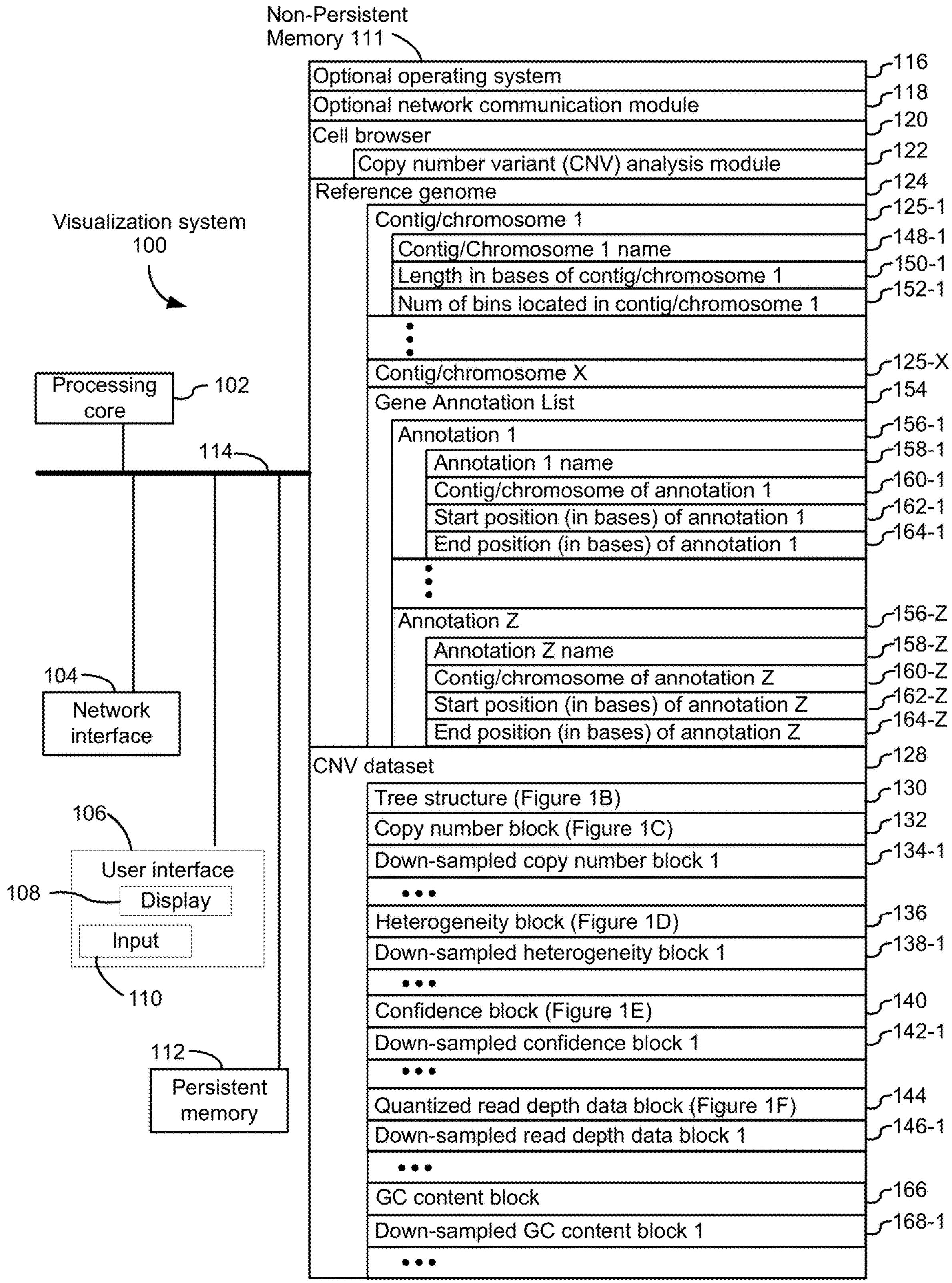

Reference will now be made in detail to embodiments, examples of which are illustrated in the accompanying drawings. In the following detailed description, numerous specific details are set forth in order to provide a thorough understanding of the present disclosure. However, it will be apparent to one of ordinary skill in the art that the present disclosure may be practiced without these specific details. In other instances, well-known methods, procedures, components, circuits, and networks have not been described in detail so as not to unnecessarily obscure aspects of the embodiments.

The implementations described herein provide various technical solutions to detect a pattern in datasets. An example of such datasets are datasets arising from sequencing pipelines that quantify gene expression in single cells as disclosed in in U.S. patent application Ser. No. 15/887,947, entitled "Methods and Systems for Droplet-Based Single Cell Barcoding," filed Feb. 2, 2018 (the '947 application), which is hereby incorporated by reference. Details of implementations are now described in conjunction with the Figures.

FIG. 1 is a block diagram illustrating a visualization system 100 in accordance with some implementations. The device 100 in some implementations includes one or more processing units CPU(s) 102 (also referred to as processors), one or more network interfaces 104, a user interface 106, a non-persistent memory 111, a persistent memory 112, and one or more communication buses 114 for interconnecting these components. The one or more communication buses 114 optionally include circuitry (sometimes called a chipset) that interconnects and controls communications between system components. The non-persistent memory 111 typically includes high-speed random access memory, such as DRAM, SRAM, DDR RAM, ROM, EEPROM, flash memory, whereas the persistent memory 112 typically includes CD-ROM, digital versatile disks (DVD) or other optical storage, magnetic cassettes, magnetic tape, magnetic disk storage or other magnetic storage devices, magnetic disk storage devices, optical disk storage devices, flash memory devices, or other non-volatile solid state storage devices. The persistent memory 112 optionally includes one or more storage devices remotely located from the CPU(s) 102. The persistent memory 112, and the non-volatile memory device(s) within the non-persistent memory 112, comprises non-transitory computer readable storage medium. In some implementations, the non-persistent memory 111 or alternatively the non-transitory computer readable storage medium stores the following programs, modules and data structures, or a subset thereof, sometimes in conjunction with the persistent memory 112:

- an optional operating system 116, which includes procedures for handling various basic system services and for performing hardware dependent tasks;
- an optional network communication module (or instructions) 118 for connecting the visualization system 100 with other devices, or a communication network;
- a cell browser module 120 that includes a copy number variant (CNV) analysis module 122 for selecting a CNV dataset 128 from persistent memory and presenting information about the CNV dataset;
- a reference genome 124 that comprises a list of contigs (or chromosomes) 125 of the reference, including length (in bases) 150 and name 148 of each contig/chromosome 125, and the number of bins 152 located within the contig, and optionally further comprising a gene annotation list 154 that includes, for each annotation 156, the annotation name 158, the contig/chromosome 160 the annotation lies on, the start position 162, in bases, of the annotation on the contig/chromosome, and the end position 164, in bases, of the annotation on the contig/chromosome; and
- a CNV dataset 128 that includes a tree structure 130, a copy number block 132, one or more down-sampled copy number blocks 134, a heterogeneity block 136, one or more down-sampled heterogeneity blocks 138, a confidence block 140, one or more down-sampled confidence blocks 142, a quantized read depth data block 144, one or more down-sampled quantized read depth data blocks 146, a GC content block 166 which includes a value of the GC percentage in each bin of the reference genome 124, and one or more down-sampled GC content blocks 168 (e.g., 168-1).

In some implementations, one or more of the above identified elements are stored in one or more of the previously mentioned memory devices, and correspond to a set of instructions for performing a function described above. The above identified modules, data, or programs (e.g., sets of instructions) need not be implemented as separate software programs, procedures, datasets, or modules, and thus various subsets of these modules and data may be combined or otherwise re-arranged in various implementations. In some implementations, the non-persistent memory 111 optionally stores a subset of the modules and data structures identified above. Furthermore, in some embodiments, the memory stores additional modules and data structures not described above. In some embodiments, one or more of the above identified elements is stored in a computer system, other than that of visualization system 100, that is addressable by visualization system 100 so that visualization system 100 may retrieve all or a portion of such data when needed.

Although FIG. 1A depicts a "visualization system 100," the figures are intended more as functional description of the various features which may be present in computer systems than as a structural schematic of the implementations described herein. In practice, and as recognized by those of ordinary skill in the art, items shown separately could be combined and some items could be separated. Moreover, although FIG. 1A depicts certain data and modules in non-persistent memory 111, some or all of these data and modules may be in persistent memory 112.

While a system in accordance with the present disclosure has been disclosed with reference to FIG. 1A, a method in accordance with the present disclosure is now detailed with reference to FIG. 2.

Block 202. One aspect of the present disclosure provides a visualization system 100. The visualization system 100 comprises one or more processing cores 102, a non-persistent memory 111 and a persistent memory 111, the persistent memory and the non-persistent memory collectively storing instructions for performing a method. A non-limiting example of a visualization system is illustrated in FIG. 1A, with further detail provided in FIGS. 1B, 1C, 1D, 1E and 1F.

Block 204. Turning to block 204 of FIG. 2, a CNV dataset 128 that comprises a plurality of compressed contiguous blocks of data is obtained. Each contiguous block of data represents a different characteristic, in a plurality of characteristics, for a plurality of cells across each bin 126 in a plurality of bins. Each bin 126 in the plurality of bins maps to a different portion of reference genome 124. The CNV dataset 128 further comprises a plurality of compressed downsampled contiguous blocks of data, each compressed downsampled contiguous block of data representing a different contiguous block in the plurality of contiguous blocks in downsampled form across the plurality of bins. In some embodiments, the CNV dataset 128 does not initially include the downsampled contiguous blocks and such downsampled contiguous blocks are formed from the corresponding contiguous blocks after the CNV dataset 128 is obtained. In alternative embodiments, the CNV dataset 128 does initially include the downsampled contiguous blocks.

The goal of analysis module 122 (e.g., Loupe scDNA Browser 1.0) is to quickly identify groups of cells with common copy number patterns, for between 1 and 100,000 cells, between 5 and 50,000 cells, or between 10 and 20,000 cells, that have been individually sequenced to explore genomic regions within clones that may have high variation, to be able to compare genomic copy number between groups of cells in particular genomic regions, and to provide enough heuristic information to allow for the determination of the quality of copy number information.

Figure 5A:
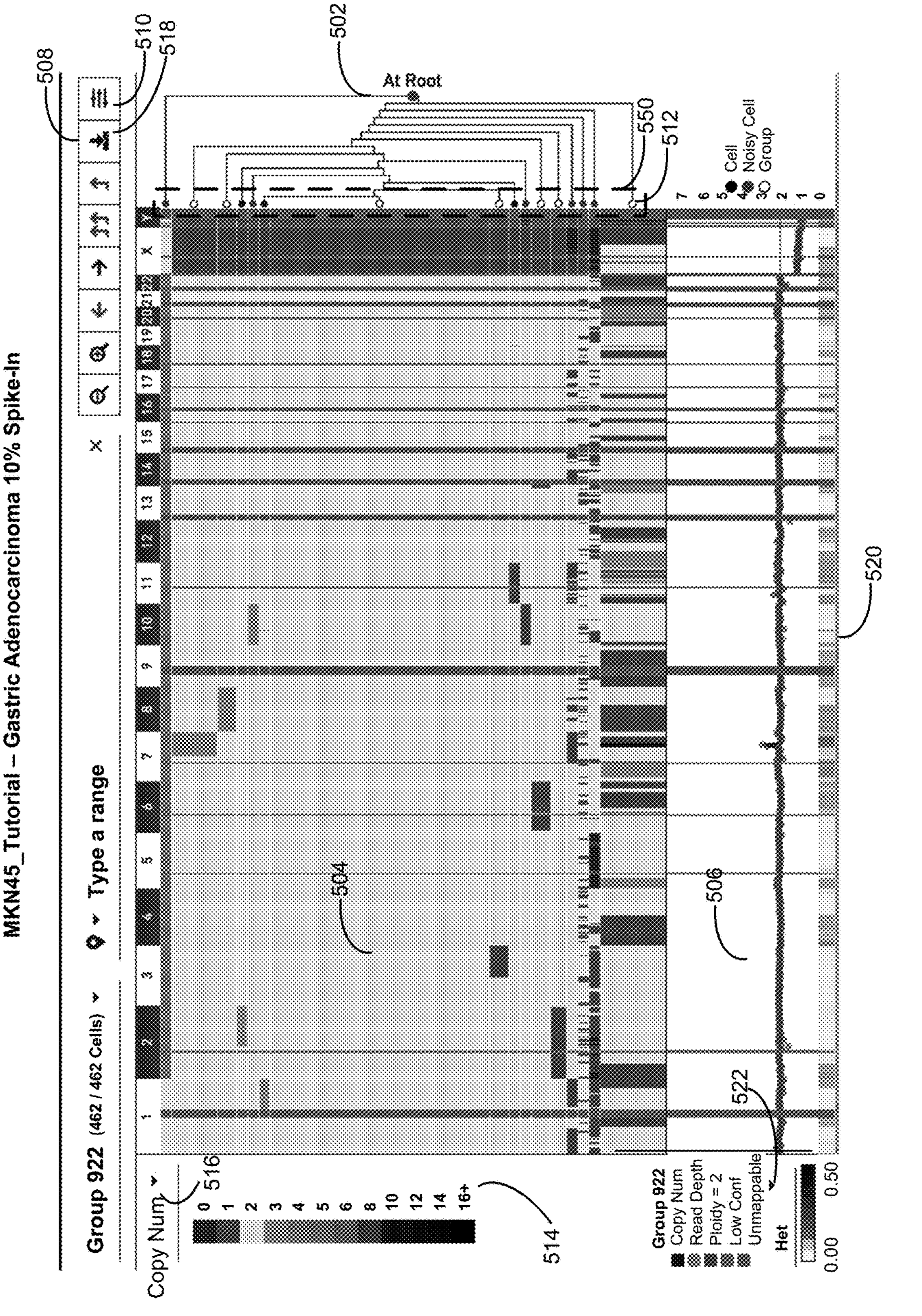
FIG. 5A illustrates a dataset in which cells are clustered on one a characteristic across the bins thereby forming a tree that includes root, intermediate, and terminal nodes, where the cells are terminal nodes and intermediate nodes have two daughter nodes, themselves being intermediate nodes or a cell, where a subset of the tree is displayed (right side of Figure) that includes the root and leaves, each leaf representing an intermediate node or a cell, and where a heat map of the characteristic is also displayed (left side of Figure), the heat map including a segment for each leaf, across the bins, and when a segment represents an intermediate node, it is an average of the characteristic across daughters of the node, and further the display of graphs of characteristics for the root across the bins (lower portion of Figure, "root panel graph") in accordance with some embodiments of the present disclosure.
Figure 5B:
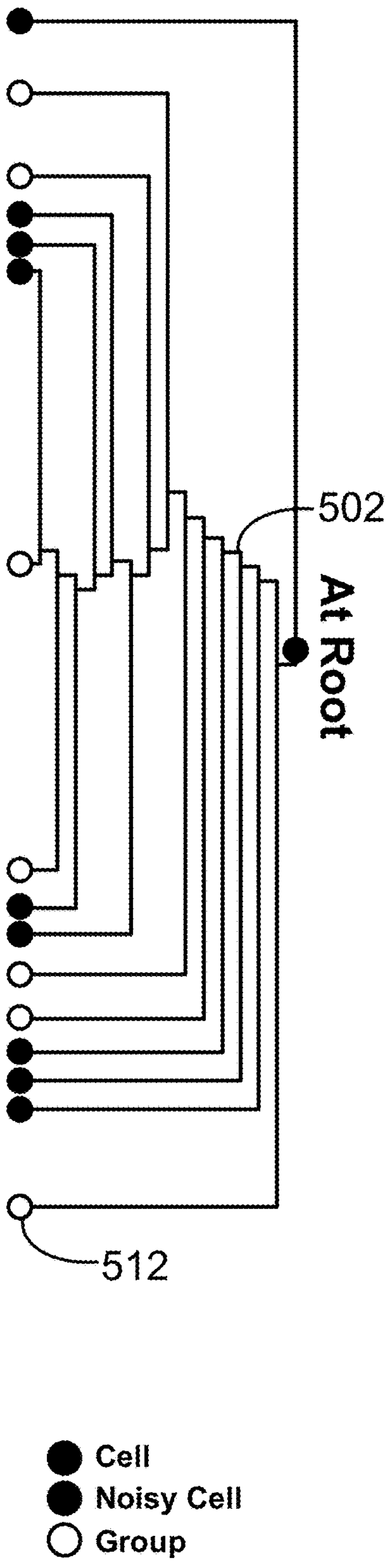
FIG. 5B provides an enlarged view of the tree illustrated in FIG. 5A.

The visualization is centered around a hierarchical tree 130 of cells, illustrated as element 502 in FIGS. 5A and 5B, and intermediate nodes. The hierarchical tree 130 is computed by the analysis module 122 as described in further detail below. In some embodiments, the CNV dataset 128 encodes single-cell CNV data (ploidy, heterogeneity, confidence, coverage/depth, GC content) into corresponding contiguous blocks of N×T data points, where N is the number of bins 126 that span the genome reference 124, and Tis the number of nodes in a tree (2C−1, where C is the computed cell count) of the dataset. In some embodiments, these blocks are row-oriented (such that two adjacent values in the array will be bin values of the same row, unless they fall on a multiple of N), and optionally compressed in block gzip format or some other form of compression.

Referring to FIG. 1C, in some such embodiments, one such block within the CNV dataset 128 is a copy number block 132. For each of 2C−1 nodes (illustrated as T nodes in FIG. 1C), the copy number block includes a copy number for each bin 124 of the reference genome 124.

Referring to FIG. 1D, in some such embodiments, another such block within the CNV dataset 128 is a heterogeneity block 136. For each of 2C−1 nodes (illustrated as T nodes in FIG. 1D), the heterogeneity block includes a heterogeneity metric for each bin 124 of the reference genome 124.

Referring to FIG. 1E, in some such embodiments, another such block within the CNV dataset 128 is a confidence block 140. For each of 2C−1 nodes (illustrated as T nodes in FIG. 1E), the confidence block includes a confidence metric for each bin 124 of the reference genome 124.

Referring to FIG. 1F, in some such embodiments, another such block within the CNV dataset 128 is the quantized read depth data block 144. For each of 2C−1 nodes (illustrated as T nodes in FIG. 1C), the quantized read depth data block 144 includes a quantized read depth data block metric for each bin 124 of the reference genome 124.

Referring to FIGS. 1C, 1D, 1E, and 1F, it is seen that, in some embodiments, each node includes a copy number vector, a heterogeneity vector, a confidence vector, and a quantized read depth vector, in the form of corresponding rows in the copy number block 132, heterogeneity block 136, confidence block 140, and quantized read depth data block 144. In some embodiments, the reference genome 124 is human. The human genome is over three gigabases long. In embodiments where this is divided into 20-kilobase bins, the copy number vector, heterogeneity vector, confidence vector, and quantized read depth vector of each node has over 150,000 elements. Yet, the most high-precision monitors have 5000 pixels, and most users will only have about around 1000 pixels of horizontal resolution. Accordingly, it is a waste of computational resources to send all 150,000 points to the front-end at the same time when visualizing this data.

Advantageously, to solve this problem, the analysis module 122 creates down-sampled representations of copy number, heterogeneity, confidence and read depth for each node. So, in addition to the N×T blocks of bin data illustrated in FIGS. 1B through 1F, the pipeline computes downsampled versions of these blocks. Thus, the analysis module 122 creates at least one form of down-sampled copy number block 134 that is a down-sampled form of the copy number block 132, at least one form of down-sampled heterogeneity block 138 that is a down-sampled form of the heterogeneity block 136, at least one down-sampled confidence block 142 that is a down-sampled form of the confidence block 140, and at least one down-sampled read depth data block 146 that is a down-sampled form of the quantized read depth data block 144.

For instance, in the case where the reference genome is human and the bin size is 20k, one form of down-sampled block samples values at 80 kb (roughly N/4×T). In some embodiments, multiple different down-sampled blocks are created for each of the blocks 132, 136, 140, and 144. For instance, in some embodiments where the reference genome is human and the bin size is 20 kb, one form of down-sampled block samples values in the corresponding full size block at 80 kb (roughly N/4×T), another form of down-sampled block samples values in the corresponding full size block at 320 kb (~N/16×T), still another form of down-sampled block samples values in the corresponding full size block at 1.28 Mb (~N/64×T), and still another form of down-sampled block samples values in the corresponding full size block at 5.12 Mb (~N/256×T). In some such embodiments, when the analysis module 122 is used to load a CNV dataset 124 into the cell browser 120, the initial values that are displayed in the user interface (e.g., heat map 504) are at the 5.12 Mb resolution level, which requires only needs 618 bins to span the entire genome.

In some embodiments, heterogeneity values in the heterogeneity block 136 are stored in floating-point format, so down-sampling to form the down-sampled heterogeneity block 138 from the full-sized heterogeneity block 136 is done in such embodiments by simple averaging of floating-points across all the bins in the heterogeneity block 136 that corresponds to a larger bin in the down-sampled heterogeneity block 138. For instance, if the down-sampling is N/4×T (where N is the number of bins needed to span the reference genome and T is the number of nodes in the tree 130), then the copy number value of four consecutive bins in the heterogeneity block 136 are averaged to form the corresponding heterogeneity value of a single bin in the down-sampled heterogeneity block 136.

It is possible that a bin may span unmapped regions. When this is the case, the unmapped values do not contribute to the averages. For example, if 64 out of 256 bins in a heterogeneity block that are averaged to form a single block in the corresponding down-sampled 5.12 Mb heterogeneity block are unmapped, then the heterogeneity average for this block will be computed from the remaining 192. If more than half of the bins in the heterogeneity block 136 that are used to form the value of a single corresponding block in the down-sampled heterogeneity block 138 are unmapped, then bins in the down-sampled heterogeneity block 138 will be unmapped (marked −1 as a symbolic value).

In some embodiments copy number and confidence values are stored as 8-bit signed integers in the respective copy number block 132 and confidence block 140, where a negative value implies an unmappable bin. In some embodiments, down-sampling of copy number and confidence to form the corresponding down-sampled copy number block 134 and down-sampled confidence block 142 is done by storing the 16-bit sums of copy number and confidence, respectively.

The down-sampled copy number for a bin in the down-sampled copy number block 134 is computed by dividing the sum of the corresponding blocks in the copy number block 132 by the zoom factor, at runtime. A sum spanning D*Xkb (where X represents bin size, e.g., 20 kb) bases is adjusted upward if there are either (D/2 or less) unmappable bins inside, or the corresponding bin in the down-sampled copy number block is at the end of a chromosome. For example, in the case where bin size in the copy number block 132 is 20 kb, if the last bin in a chromosome spans 128 20 kb bases, instead of 256, the sum is doubled, such that the sum/zoom level calculation still works, even though the bin only spans 128 20 kb blocks. The same thing would happen when there are 64 unmappable bins. The goal is to keep downsampled copy number as 16-bit integers, which saves space over encoding floats.

The down-sampled confidence values for a bin in the down-sampled confidence block 134 is computed by dividing the sum of the corresponding blocks in the confidence block 140 by the zoom factor, at runtime. A sum spanning D*Xkb (where X represents bin size, e.g., 20 kb) bases is adjusted upward if there are either (D/2 or less) unmappable bins inside, or the corresponding bin in the down-sampled confidence block 142 is at the end of a chromosome. For example, in the case where bin size in the confidence block 140 is 20 kb, if the last bin in a chromosome spans 128 20 kb bases, instead of 256, the sum is doubled, such that the sum/zoom level calculation still works, even though the bin only spans 128 20 kb blocks. The same thing would happen where there are 64 unmappable bins. As was the case for copy number, the idea is to keep downsampled confidence as 16-bit integers, which saves space over encoding floats.

In some embodiments, read depths are encoded in the quantized read depth block 144 and downsampled to form the down-sampled read depth data block 146 in a special manner, to try to reduce file size footprint of the CNV dataset 128. The normalized read depth at a particular bin in the quantized read depth database block 144 is the number of sequencing reads that were found within a bin, adjusted for potential percent GC bias. This number can be converted to an "imputed copy number," which is the read coverage at that bin, divided by average read depth at each bin, times the average ploidy of the node. Here, the number of sequencing reads in a bin is the number of sequencing reads that, when aligned to the reference genome 124, fall within the genomic region of the bin. Read depth is adjusted for % GC bias on the basis that GC-rich regions are harder to sequence with some forms of high-throughput sequencing such as Illumina systems. As such, assuming a uniform distribution of read molecules across the genome going into a sequencer, it is to be expected that the number of correctly read and aligned reads coming out of the sequencer would be lower in regions with high percent GC content. The observed read coverage from the sequencer is thus adjusted upward in high percent GC regions to form a corrected read depth within a bin. For more information, see Example 2, "Correcting for GC bias," below. The "imputed copy number" referenced above refers to the total number of reads across an entire cell or group of cells associated with a node, and an (average) copy number for the entire cell or group of cells for the node as determined by the pipeline. The imputed copy number is thus the number of reads in a bin, divided by the average number of reads per mappable bin, multiplied by the ploidy of the node. To illustrate, consider the case where the node represents a single cell that has 150,000 bins, 900,000 total reads, and a ploidy of 2. Consider the copy number of bins A and B:

Bin A has normal (45%) GC content and 6 reads. Since the average number of reads per bin is 6 (900,000), and there are 6 reads in the bin, the imputed copy number across that bin is also 2, the same as the ploidy of the cell.

Bin B has high (63%) GC content and 10 reads. The GC correction may imply that 12 reads were in that bin instead. The imputed copy number is then 4—since 12/6=2.

In some embodiments, the analysis module 122 quantizes the imputed copy number into one of 252 int8 values, which are weighted in density toward the 0-8 region. The quantization can represent ploidies between 0 and 8 at 0.04 resolution, between 8 and 16 at 0.2 resolution, between 16 and 24 at whole integer resolution, and has a symbolic "imputed copy number >24" value. Approximate read depths are converted back at runtime by dequantizing the stored integer value to the imputed copy number, dividing by the average copy number of the node, and multiplying by the average read depth. In some embodiments, average copy numbers and read depths of each node are also stored in the CNV dataset 128, as well as percent GC content for the entire reference.

In some embodiments, the CNV dataset 128 stores information about the contigs of the reference 125, gene annotations 156 from the reference, and the structure of the tree 130 (including barcodes of each node the dataset 128). In some embodiments the contiguity, gene and tree information are stored as JSON objects. In some embodiments, the CNV dataset includes the reference/genome data structure 124 illustrated in FIG. 1A. In some embodiments, the CNV dataset stores a map between the barcode suffix (also known as the "GEM well") and the source sample corresponding to that suffix. For instance, in some such embodiments, all barcodes with the same suffix (e.g., the "1" in AAACTTATAAAGATAA-1) are from the same original sample. Thus, in such instances an example map can be "{1: 'Sample A', 2: 'Sample B'}. Each GEM well is a physically distinct set of GEM partitions, but draws barcode sequences randomly from the pool of valid barcodes, known as the barcode whitelist. To keep the barcodes unique when aggregating multiple libraries, in some embodiments, a small integer (called a GEM well suffix) identifying the GEM well is appended to the barcode nucleotide sequence, and the nucleotide sequence plus ID serves as the unique identifier. For example, AGACCATTGAGACTTA-1 and AGACCATTGAGACTTA-2 are distinct cell barcodes from different GEM wells, despite having the same barcode nucleotide sequence.

Figure 1B:
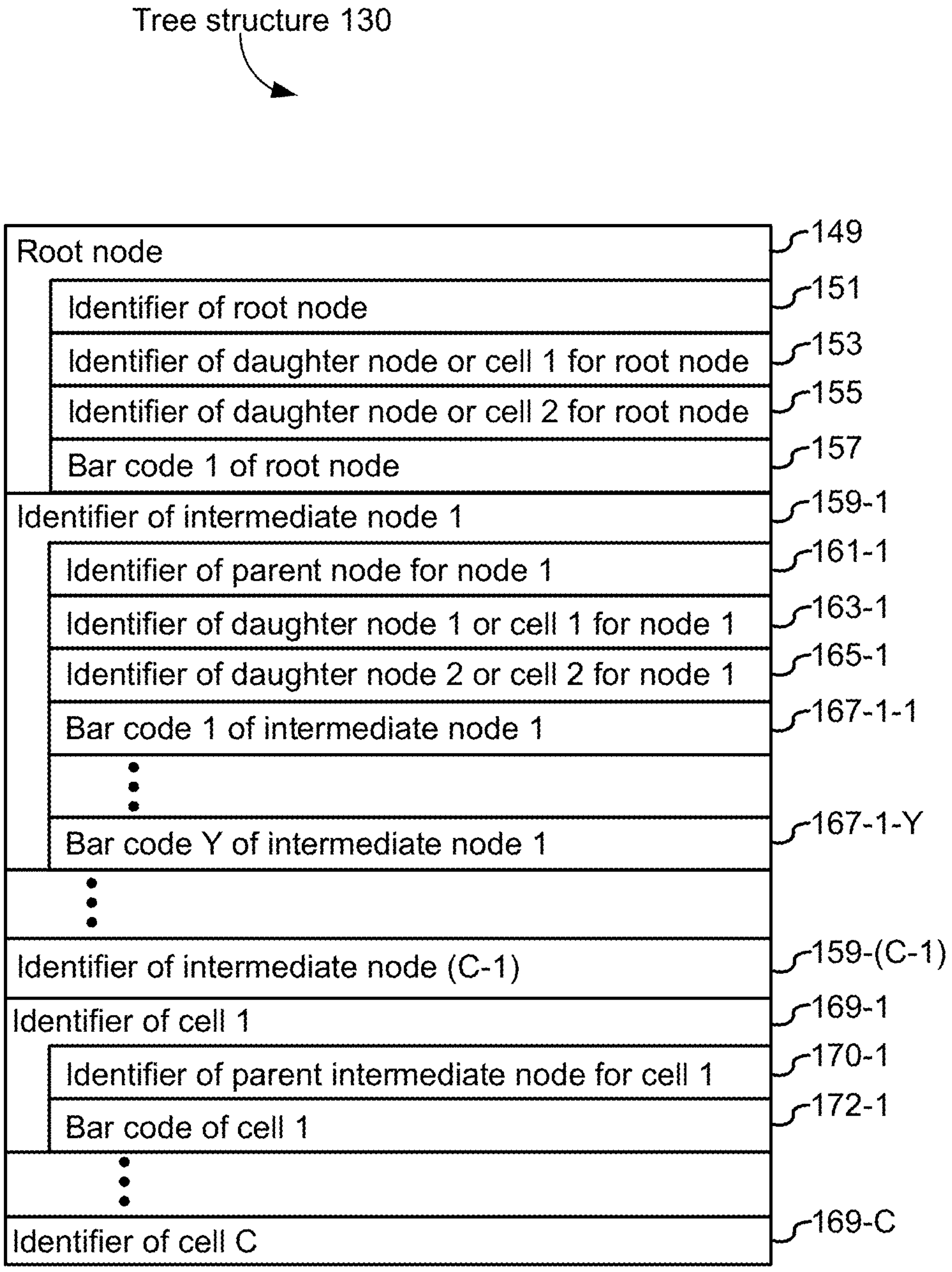

The plurality of cells represented by a CNV dataset 128 is clustered based upon a characteristic, in a first contiguous block in the plurality of blocks, across each respective bin in the plurality of bins thereby forming a tree structure 130 that includes a root node 149, a plurality of intermediate nodes 159 (e.g., 159-1, 195-(C−1)), and a plurality of cells 169 (e.g., 169-1, . . . , 169-C). In some embodiments, the first contiguous block is the copy number block and the characteristic is copy number. Referring to FIG. 1B, the respective cells 169 in the plurality of cells constitute terminal nodes in the tree structure 130 and each intermediate node 159 has two daughter nodes (163, 165, e.g., 163-1, 165-1), each daughter node being an intermediate node or a cell. Thus, upon clustering across the copy number values of bins in the copy number block, a tree structure 130 having a root node 149, intermediate nodes 159 and cell (terminal) nodes 169 is formed. The root node 149 has an identifier 151 for itself, as well as an identifier of a first daughter node or cell 153 and a second daughter node or cell 155. The root node further includes a barcode 157 obtained from the CNV dataset 128 that represents the source of the sequence reads that are associated with the root node. Each intermediate node 159 has an identifier of its parent node 161 (e.g., 161-1), as well as an identifier of a first daughter node or cell 163 and a second daughter node or cell 165. Each intermediate node further includes one or more barcodes 167 (e.g., 167-1-1, 167-1-Y) obtained from the CNV dataset 128 that represent the source of the sequence reads that are associated with the intermediate node. Each cell 169 has an identifier of its parent node 170, as well a barcode 172 obtained from the CNV dataset 128 that represent the source of the sequence reads that are associated with the cell. In some embodiments, each individual node (root node 149, intermediate nodes 159) in the tree may also include an additional label, which gives semantic meaning to subtrees. For instance, in some embodiments these labels are added after some analysis of the original dataset. In typical embodiments, these labels occur in an upstream pipeline that put together the CNV dataset. Moreover, in some embodiments, a user may choose to label the nodes of a subtree within the disclosed interface. For instance, a user may choose to label the nodes of a subtree with the label "Cancer Cells," based on exhibition of aberrant copy number presentation of nodes within that subtree. Non-limiting exemplary details of how sequence reads are obtained using single cell sequencing in some embodiments are set forth in Example 1 below.

Referring to FIG. 1B, the root node 149, intermediate nodes 159 and cells 169 each serve as nodes in the tree structure and the root node and each intermediate node has two daughter nodes. Accordingly, there are 2C−1 nodes in the tree structure 130, where C is the calculated number of cells represented by the CNV dataset 128. In some embodiments, each node in the tree has the following vectors of information, where B is the number of bins needed to span the entire genome of the sample:

B copy number values
B heterogeneity score
B confidence score
B normalized read depths As discussed above, these vectors for a respective node are represented as the row corresponding to the respective node in the copy number block 132, heterogeneity block 136, confidence block 140, and quantized read block 144 of FIGS. 1C through 1F, respectively. In addition, in some embodiments, each node contains four additional sets of downsampled vectors to support more rapid visualization when viewing large stretches of the genome, as discussed above.

As discussed above, the tree structure 130 contains C leaves, where C is the cell count as determined by the analysis module 122. The analysis module 122 then builds a tree with 2C−1 nodes, made of C cells and C−1 intermediate nodes. An intermediate node will have the same shape of information as the leaves. At a high level, cells with similar genome-wide copy number patterns should have a common intermediate node ancestor. The farther up the tree, the more disparate the copy number patterns siblings are expected to be from each other. The root node's two children are likely to be quite different unless the entire sample is homogeneous.

Figure 4:
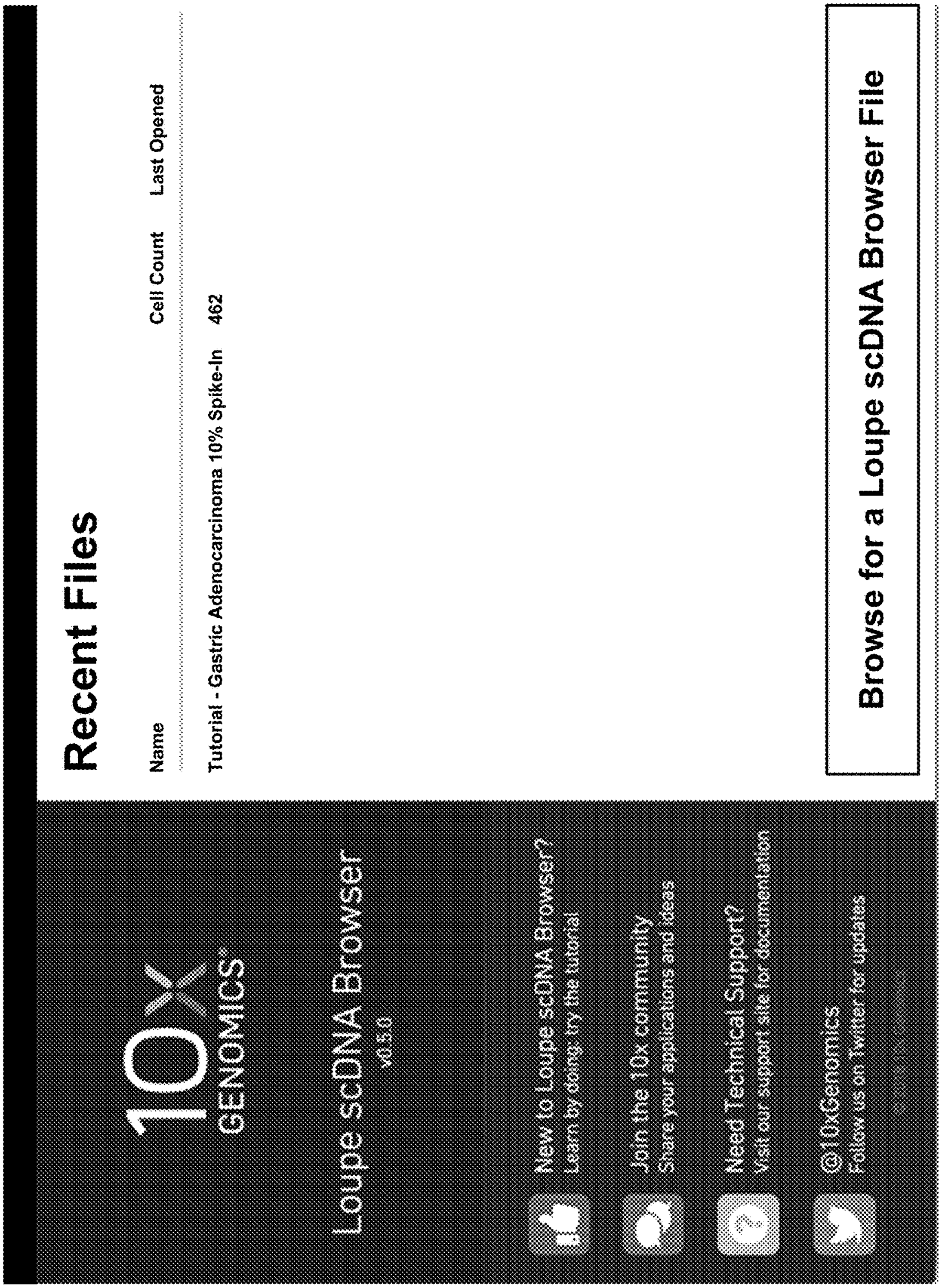
FIG. 4 illustrates obtaining a dataset in accordance with some embodiments.

The analysis module 122 provides advantageous ways of visualizing the tree structure 130 and other data in the CNV dataset 128 in order to ascertain properties of the data with the dataset. Referring to FIG. 4, a dataset 128 is loaded using interface 402. Referring to FIG. 5A, the visualization has three major components: a subset 502 of the tree 130 rooted at the node R (FIG. 5A, at right, block 206 of FIG. 2, also illustrated in FIG. 5B), a heatmap 504 of information for N of R's children (FIG. 5A, at left, block 208 of FIG. 2), and a visualization 506 of R's data vectors (FIG. 5A, at bottom, block 210 of FIG. 2). A user can alternate between displaying copy number and heterogeneity scores in the heatmap, as well as configure how many children should be displayed concurrently in the heatmap 504. The user can use the navigation panel 508 to recenter the tree 502 around a particular intermediate node, cell or barcode, to zoom in and out, to navigate to a particular genomic region or to a single gene, or to go back/forward in history, or to the top of the tree. There are also facilities for exporting information, for changing both heatmap 504 and single-node visualization settings.

Referring to FIG. 4, when opening the analysis module 122 for the first time, a recent history list, the most recently opened files, is provided and a tutorial dataset if the user has not opened any CNV datasets 128 yet. Clicking on an available dataset 128 loads the dataset into non-persistent memory 111 from persistent memory 112. The dataset used in FIGS. 5 through 11 is a spike-in of a known gastric adenocarcinoma tumor cell line into a line of diploid cells. One group (group 920) shows the known copy number pattern associated with the tumor cell line.

In some embodiments, the analysis module 122 has the following navigation state: the current root node, and the current genomic region highlighted. When loading a CNV dataset 128, information for the entire genome, anchored at the root is shown, as illustrated in FIG. 5A.

In some embodiments, the default setting is to show N=16 intermediate nodes downward from the root. In some embodiments, the default setting is to show N=32 intermediate nodes downward from the root. All the nodes are not shown, and the maximum concurrent shown nodes is 512 in some embodiments, because of visual constraints. One cannot see information about thousands of individual cells in only hundreds of pixels. The value of N can be changed by clicking on the settings button (navigation panel, affordance 510).

In some embodiments, the subtree generation heuristic is as follows: starting at the current root, expand the node with the most leaves (nodes with no children, also termed an "external node"). The first iteration will expand the root into R1 and R2—then either R1 or R2 will be expanded depending on which has more leaves . . . until there are N intermediate nodes touched. An intermediate node only has two children.

When expanding in the visualization, in some embodiments the sibling with the higher average copy number across the plurality of bins of the reference sequence will be placed above its sibling. Note that, in such embodiments, when expanding siblings, a child node of the top sibling (R1) may have lower ploidy than a child node of the bottom sibling (R2), but the R1 child will still appear above the higher R2 child.

When expanding in the visualization, in alternative embodiments the sibling with the higher average copy number across the plurality of bins of the reference sequence will be placed below its sibling.

In some embodiments, referring to FIGS. 5A and 5B, the vertical space allocated to each node in the display tree 502 is determined by the number of leaves (from the subset of cells C) it has in the tree structure 130. For instance, in some embodiments the vertical space allocated to each node in the display tree 502 is proportional to the square root of the number of leaves (from the subset of cells C) it has in the tree structure 130. In other embodiments, the vertical space allocated to each node in the display tree 502 is linearly proportional to the number of leaves (from the subset of cells C) it has in the tree structure 130. In some embodiments, the linear spacing of the nodes is optimized for "interestingness"—to highlight variation in smaller groups. In alternative embodiments, each node is given the same amount of vertical space in panel 500. In some embodiments, the setting affordance 510 leads to a menu that allows for a user to toggle between a "linear display" (which allocates vertical space in direct proportion to the number of leaves underneath each node) and the above-described square root setting. In some embodiments, other display metrics are used to determine the amount of vertical space allocated to each node in the display tree, such as a logarithm ($\log_2$, $\log_{10}$, etc.) of the number of leaves under a given intermediate node. When determining the number of leaves under a particular node, the leaves under each of the two immediate daughter nodes of the node are counted.

Figure 15:
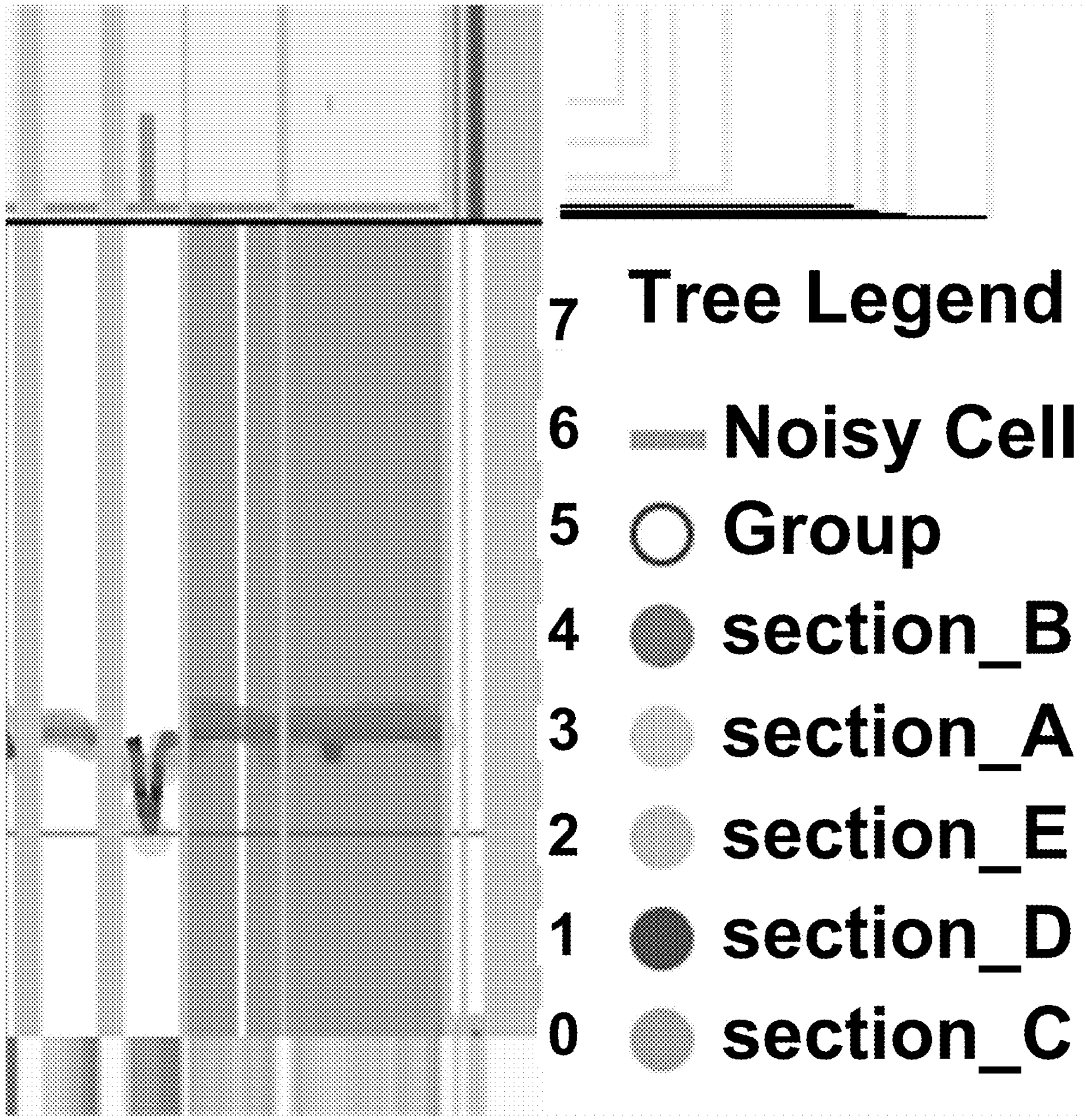
FIG. 15 illustrates a color key for nodes with the same semantic labels in a tree in accordance with an embodiment of the present disclosure.

In some embodiments, analysis module 122 provides a number of ways to navigate the tree 502. In some embodiments, the visible tree has a circle, or other mark (e.g., square, star, etc.) at each node. Clicking on a mark for a particular node will re-root the visible tree 502 at that particular node. For example, clicking on the Group 920 mark (element 512) will change the focus to the 35 cells within that group. In such a situation, element 512 will become the new root node. When viewing a tree made of multiple samples (e.g., GEM wells), the marks (e.g., circles) at each node will be color coded. Each individual sample (or barcode suffix, (e.g., the "1" in AAACTTATAAAGATAA-1) as discussed above in conjunction with FIG. 1, will have a constituent color. Nodes at which greater than 50% of the leaves came from a single sample will be drawn in the color for that sample. In some embodiments, if there is no majority, the node will be colored a default color, such as black. In some embodiments, when viewing a tree with semantically labeled nodes, each labeled node will have a constituent color, in order to more easily pick out interesting subtrees. In some embodiments, all nodes with the same label will have the same color or pattern. Any color or pattern coding, be it from multiple samples, or semantic labels, is shown in a key (e.g., at the bottom right of the browser window, to the right of the node panel as illustrated in FIG. 15. Hovering over an element in the legend will highlight in the tree the currently visible nodes that pertain to that label, or sample.

Referring to FIGS. 5A and 5B, the subset 502 of the tree is displayed on a first portion of the screen. The subset includes the root node and a plurality of leaves. These leaves are the intermediate nodes and/or cells in box 550 of FIG. 5A. Each node in the plurality of leaves represents an intermediate node in the plurality of intermediate nodes or a cell in the plurality of cells. Although the intermediate nodes in box 550 of FIG. 5A in the full tree structure 130 contain child nodes, such child nodes are not displayed in subset 502 and thus, in the context of subset 502 displayed in FIGS. 5A and 5B, such child nodes are referred to as leaves.

Figure 6:
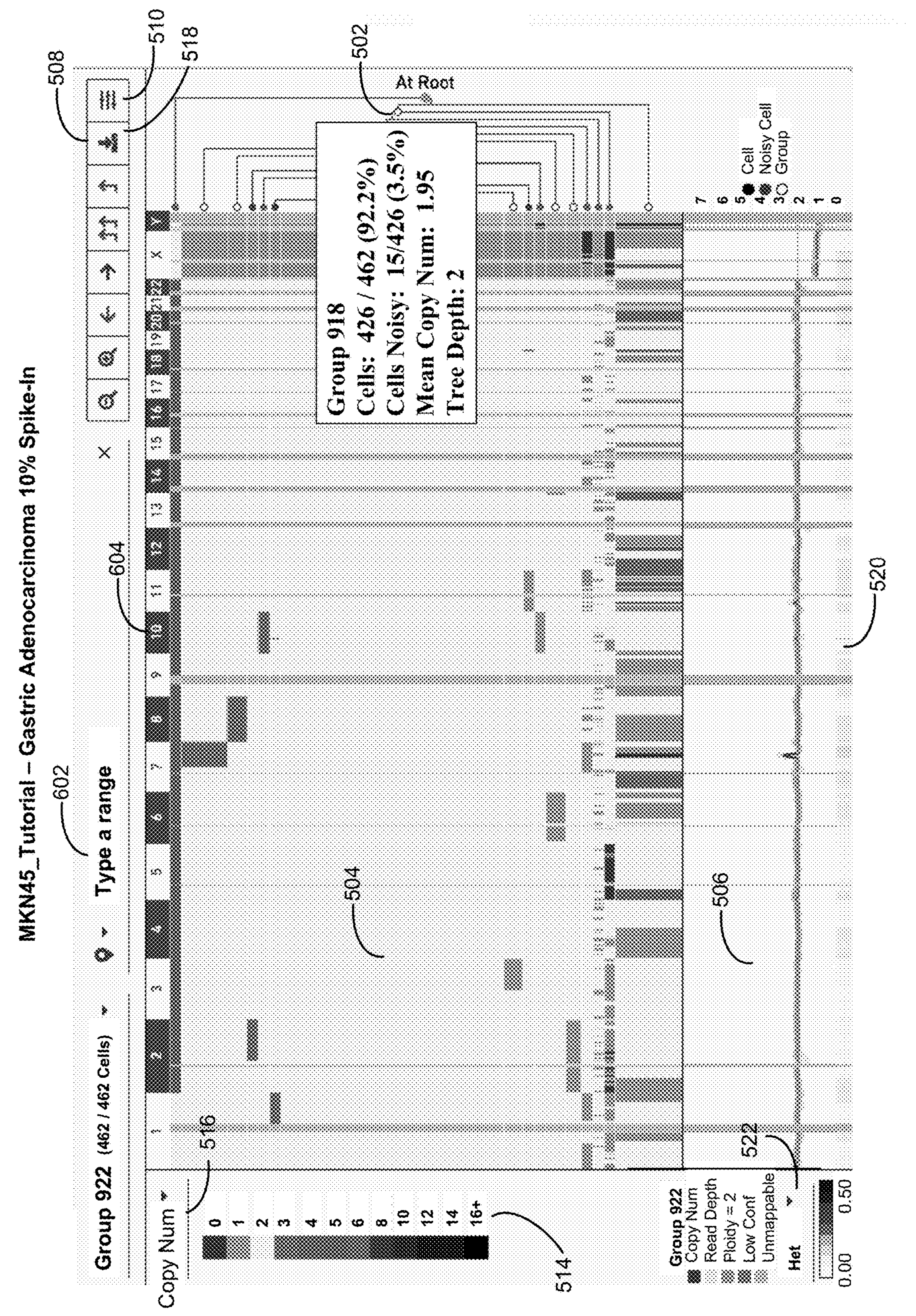
FIG. 6 illustrates obtaining information for a node in the tree by hovering over the node in accordance with an embodiment of the present disclosure.
Figure 16:
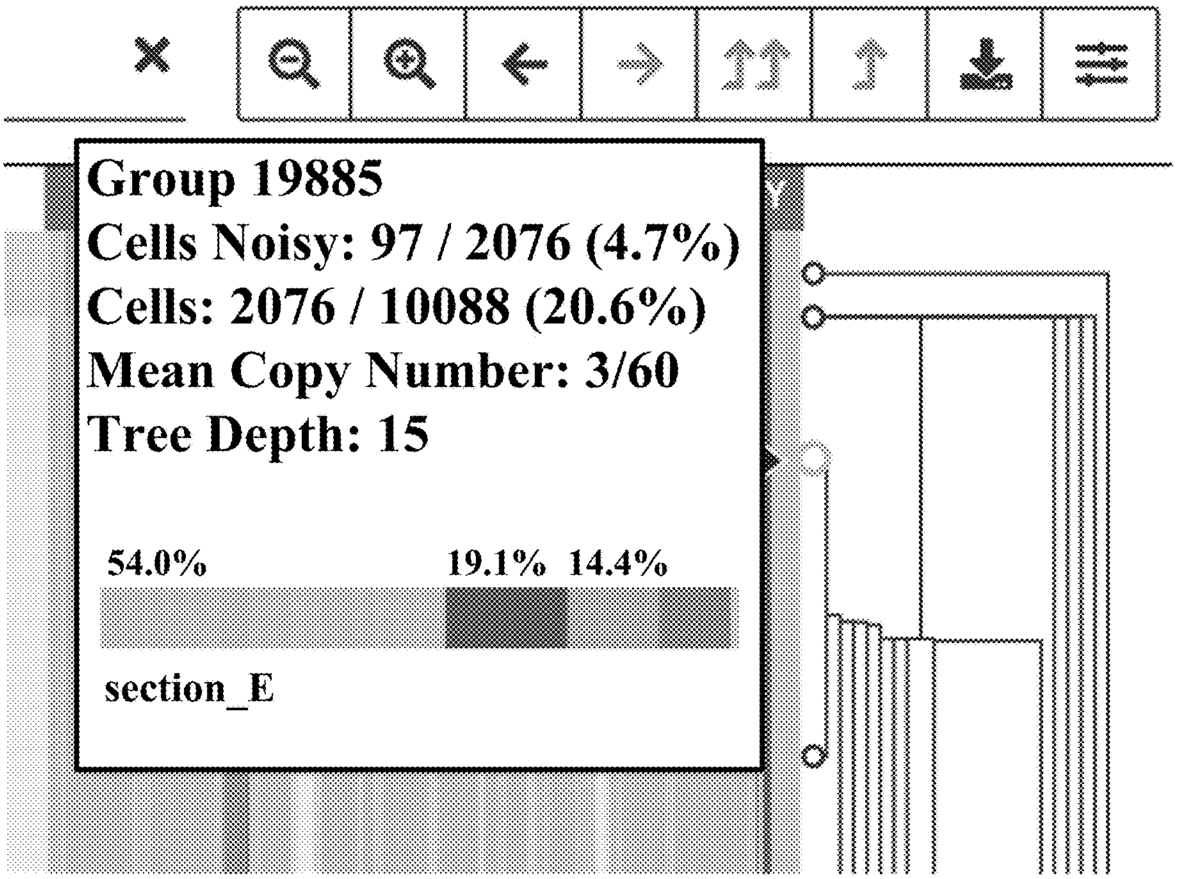
FIG. 16 illustrates a color-coded sample makeup of the subtree centered at a node in accordance with an embodiment of the present disclosure.

Referring to FIG. 6, a user can click on intermediate nodes in the visible tree by hovering over intermediate nodes and clicking on the resulting circle (or other form of mark the denotes the selected intermediate node). A user can also use the top left affordance 602 to type in a group number, cell number, or barcode (e.g., "ATAG . . . ") if the user knows the barcode of the cell of interest. In each case, the tree 502 will be rerooted at the new node. In some embodiments, as illustrated in FIG. 16, when looking at a multi-sample dataset (e.g., one that includes cells from multiple gem wells), hovering over each individual node will reveal the color-coded sample makeup of the subtree centered at that node, and include the sample name if the majority of leaves at the subtree rooted at that node came from the same original sample. For instance, in FIG. 16, when considered in conjunction with the key code of FIG. 15, the selected node includes 54 percent "Section_E" cells, 19.1 percent "Section_D" cells, 14.4 percent "Section_C" cells and trace amounts of "Section_B" and "Section_A" cells. Since, the majority of leaves at the subtree rooted at that the selected node are labeled "Section_E" cells, the selected node is labeled Section_E as illustrated in FIG. 16. Returning to FIG. 6, in some embodiments, the root nodes of labeled subtrees may be searched for in affordance 602. For instance, a user can navigate to the semantically labeled "Cancer Cells" root described above by typing "Cancer Cells" in the search box 602, and clicking on the "Cancer Cells" result.

In some embodiments, the analysis module provides users with the ability to navigate to individual regions of the genome. In some embodiments, referring to FIG. 6, a user can click on a chromosome affordance 604 above the heatmap to zoom into a particular chromosome. For instance, if the user selects chromosome "8" using the chromosome affordance 604 which provides an icon for each of the 22 human autosomes, an icon for the x chromosome, and an icon for the y chromosome, the tree 502, heat map 504, and graphs 506 are limited to the display of copy number, heterogeneity, confidence, and read depth information in the CNV dataset 128 from sequence reads that map onto human chromosome 8.

Figure 7:
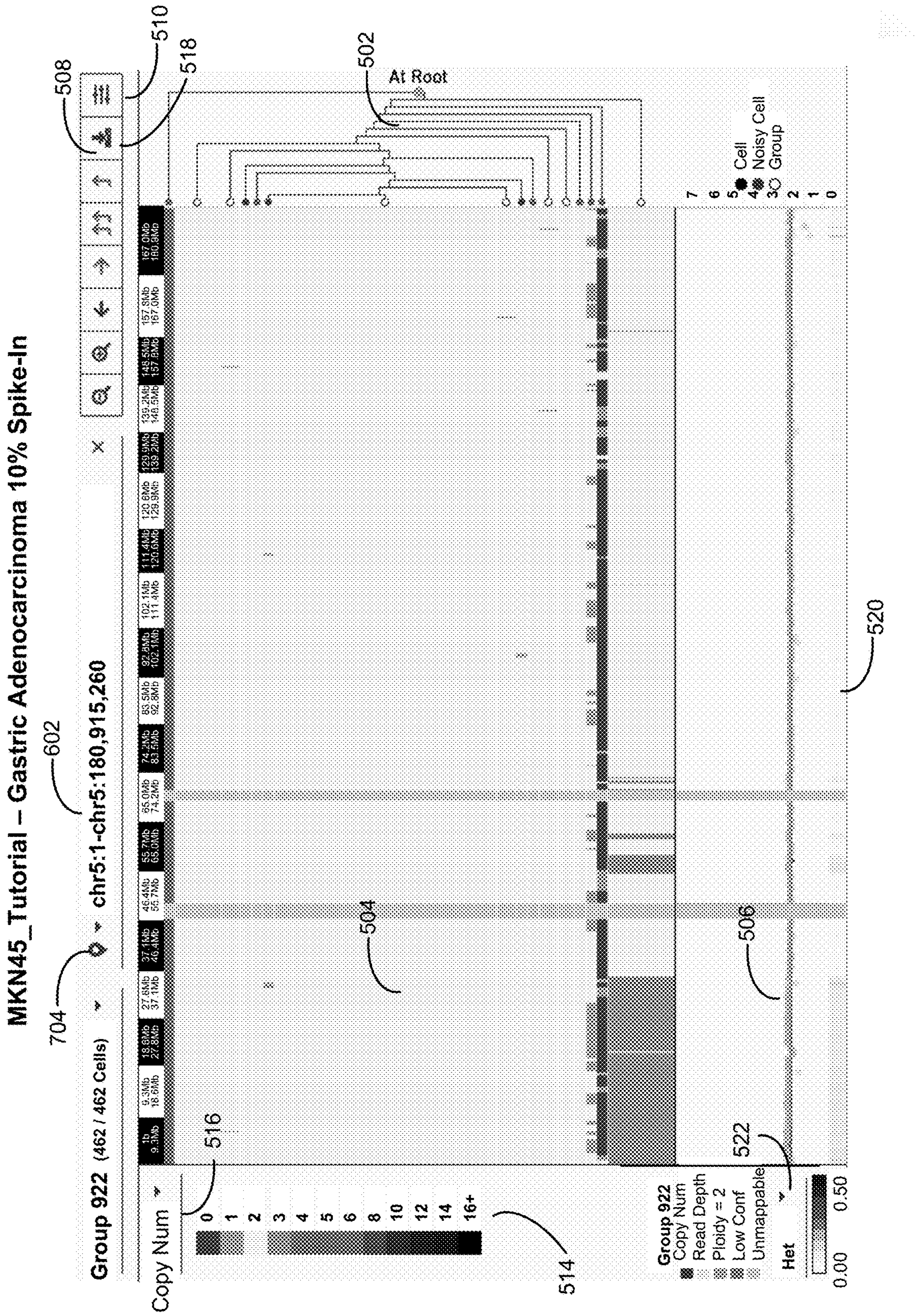
FIG. 7 illustrates selection of a chromosome label to zoom into a particular chromosome, or region within a chromosome in accordance with an embodiment of the present disclosure

In some embodiments, referring to FIG. 7, a user can specify a region of a chromosome using affordance 602 above the heatmap 504 to zoom into a particular chromosome. For instance, if the user specifies chr5:1-chr5:180,915,260 using the affordance 602, the tree 502, heat map 504, and graphs 506 are limited to the display of copy number, heterogeneity, confidence, and read depth information in the CNV dataset 128 from sequence reads that map onto this portion of the reference genome 124. As illustrated in FIG. 7, the labels change to subregions of the specified portion of the reference genome once display has been zoomed into a particular chromosome, contiguity, or subregion of the reference genome 124.

In some embodiments, the analysis module 122 permits a user to zoom in by dragging within the heatmap 504 or node visualization 502. A user can type a genomic region (e.g., "chr11:1-10000000") when the map icon is selected as illustrated in FIG. 7. A user can type an autocompleted gene after selecting "Gene" from the dropdown 704 to the left of affordance 602.

In some embodiments, the affordances on top of the navigation panel allows a user to go back/forward to the previous viewed location, to return to the root, or to go up one level in the tree (when applicable).

Heatmap Information. In some embodiments, the heatmap 504 displays either copy number or heterogeneity of the currently visible nodes across the specified range of the reference genome 124. In some embodiments, the heatmap 504 shows copy number by default. The legend 514 of the heat map (copy number in FIG. 5, heterogeneity in FIG. 8) is to the left of the heatmap 502 in FIGS. 4-11, and, referring to FIG. 5, the color of a node's (y-axis) bar at a genomic position (x-axis) is its copy number at that position in FIG. 5. Referring Figure to 8, where the heat map 502 shows heterogeneity rather than copy number, the color of a node's (y-axis) bar at a genomic position (x-axis) is its heterogeneity at that position. Above legend 514, a user can toggle between copy number and heterogeneity using affordance 516.

Copy number. Regarding copy number, for a single cell, the copy number for a region should be roughly proportional to the number of sequence reads in that region compared to the average number of read coverage across the genome for that cell. The copy number of intermediate nodes is calculated by considering the joint read coverage of all children of that node. It is a plurality (consensus) for that node.

Figure 8:
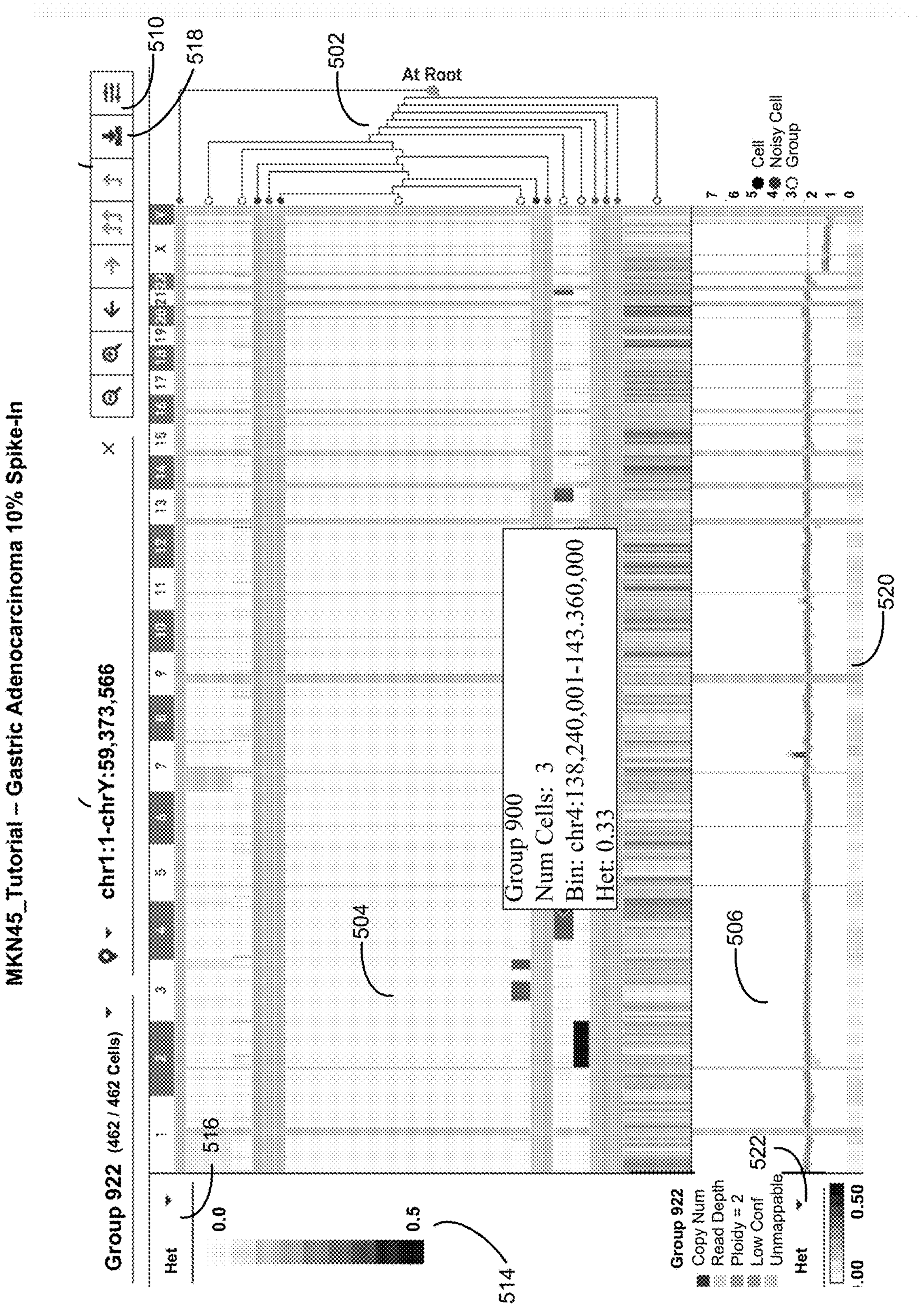
FIG. 8 illustrates obtaining information for a region in the heat map by hovering over the region in accordance with some embodiments of the present disclosure.

Heterogeneity. Regarding heterogeneity, the heterogeneity of a particular intermediate node is the fraction of child leaves/cells of that node that disagree with the consensus copy number at that location. This can be visualized by selecting "Heterogeneity" from affordance 516. When this is done, as illustrated in FIG. 8, at group 900, in chromosome 4, there are three cells. The copy number call is 2 at chromosome 4. When zooming in (not shown), it is seen that one of these cells has a copy number of 1 at chromosome 4. Thus, the heterogeneity score there is 0.33 because 1 of 3 cells in that group has a copy number that is not 2.

Returning to copy number, in some embodiments analysis module 122 provides some functionality that makes it easier to handle high-ploidy populations. In such embodiments, clicking on any square in the affordance 514 will bring up a menu having three options—"Show only Copy Number X" (where X is the numeric value of the square clicked on in affordance 514, e.g. "6"), "Set White Point," and "Show All Copy Numbers." The menu selection "Show Only Copy Number X" will hide values that do not equal the selected value. The menu selection "Show All Copy Numbers" reverses this action. The menu selection "Set White Point" will recenter the gradient around the selected value, which is useful for tetraploid or high-ploidy cancer samples.

In some embodiments, the color dark gray in both the heatmap 504 and single-node panel 506 indicate regions for which a copy number could not be determined. These include unmappable regions, such as centromeres, the Y chromosome for human female samples, or for more technical reasons.

Figure 9:
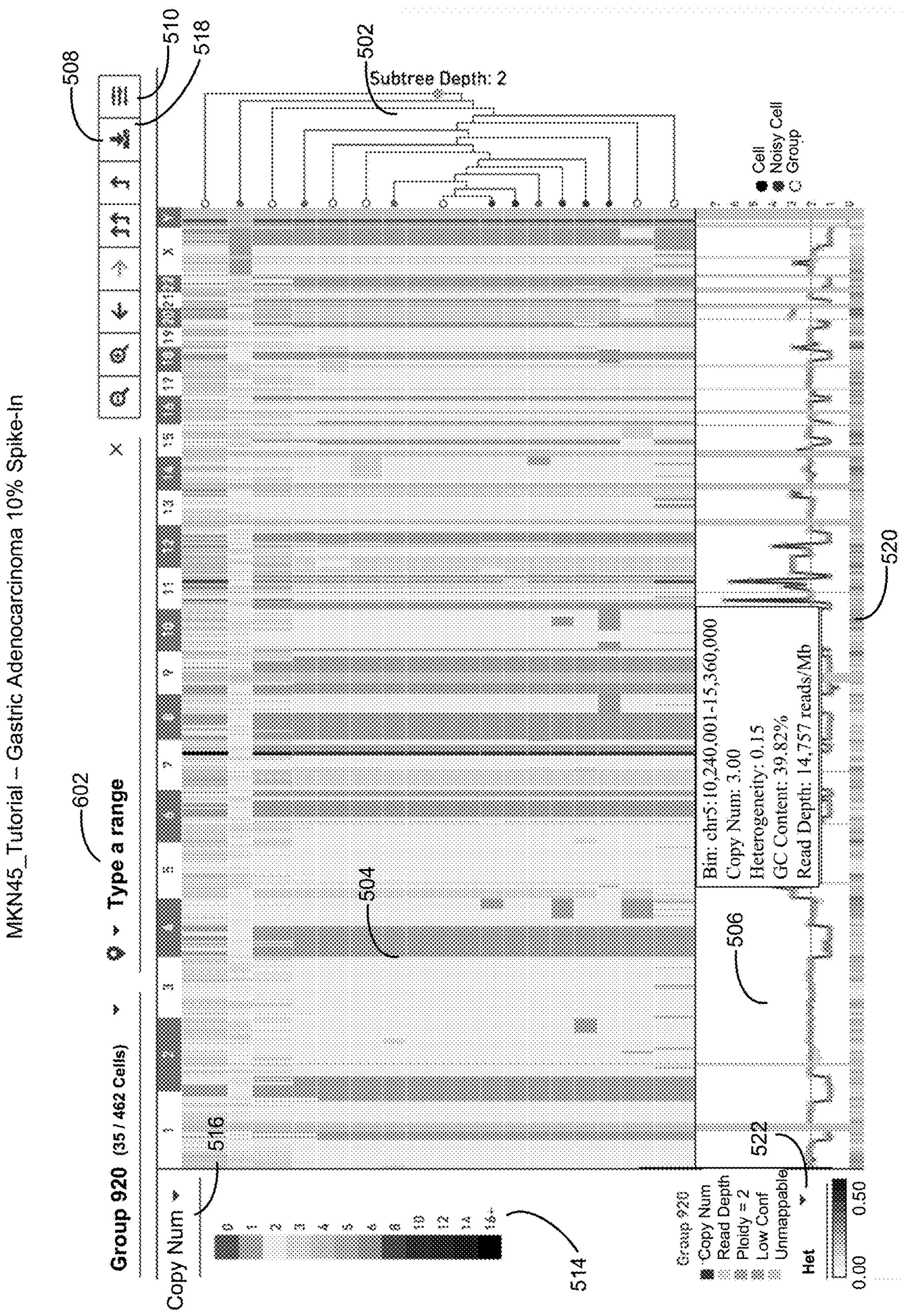
FIG. 9 illustrates obtaining information for a region in the graphs by hovering over a region in graphs in accordance with some embodiments of the present disclosure.

Node/Root Panel. Referring to FIG. 9, the bottom third of the visualization displays information 506 about the current root of tree 502. Note that the current root of tree 502 is not necessarily the absolute root of tree structure 130 (root node 149), because, as discussed above, a user can change the focus (root node) of tree 502 to be any of the intermediate nodes 159 of tree structure 130, or for that matter, in some embodiments, any of the cells 169 of the tree structure 130. The central focus of the root panel 506 is the copy number line (black) and read depth circles. This shows the copy number calls for the currently-selected root node, and the approximate read coverage/megabase at each bin. The copy number values range between 0 and 8 are always shown in the line graph. As illustrated in FIG. 9, hovering over the graph 506 will show the position, copy number, heterogeneity, % GC content, and read depth/coverage at that position. In addition, a green line is drawn that corresponds to the "whitepoint" as selected in the heatmap affordance 514.

Figure 10:
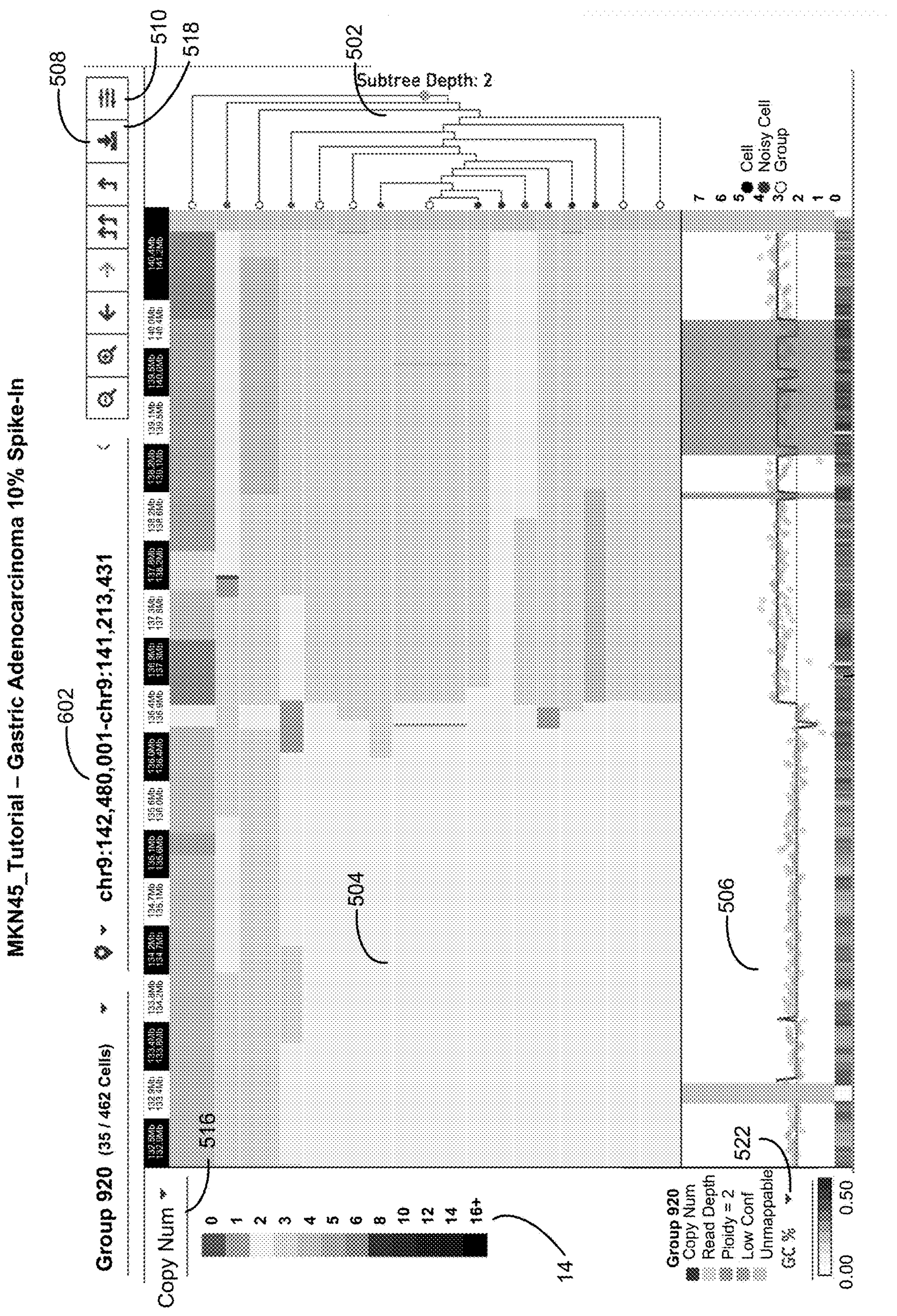
FIG. 10 illustrates how the root panel graph will have gray vertical bars where the region is unmappable, and red bars in areas where CNV call confidence is low, primarily due to read coverage variability in accordance with some embodiments of the present disclosure.

Below the line graph 506 is a colorbar 520, which can represent either the heterogeneity of that node (e.g., as illustrated in FIG. 5), or the % GC content (e.g., as illustrated in FIG. 10) of the reference at that region. A user can change between these two options by selecting the dropdown affordance 522. In some embodiments heterogeneity ranges from blue (low heterogeneity)->purple (high heterogeneity, and % GC content is yellow (low % GC content)->orange (high % GC content). The % GC content is shown to indicate to the user whether a particular copy number variant call may have been influenced by being in a high-GC content region, which can be harder to sequence with some sequencing chemistries.

In some embodiments, the root panel graph 506 has gray vertical bars where the region is unmappable, and red bars in areas where copy number variance call confidence was low, primarily due to read coverage variability. Examples of this are seen in the right side of chromosome 9 (FIG. 10, zoomed into the last regional bin).

Figure 11A:
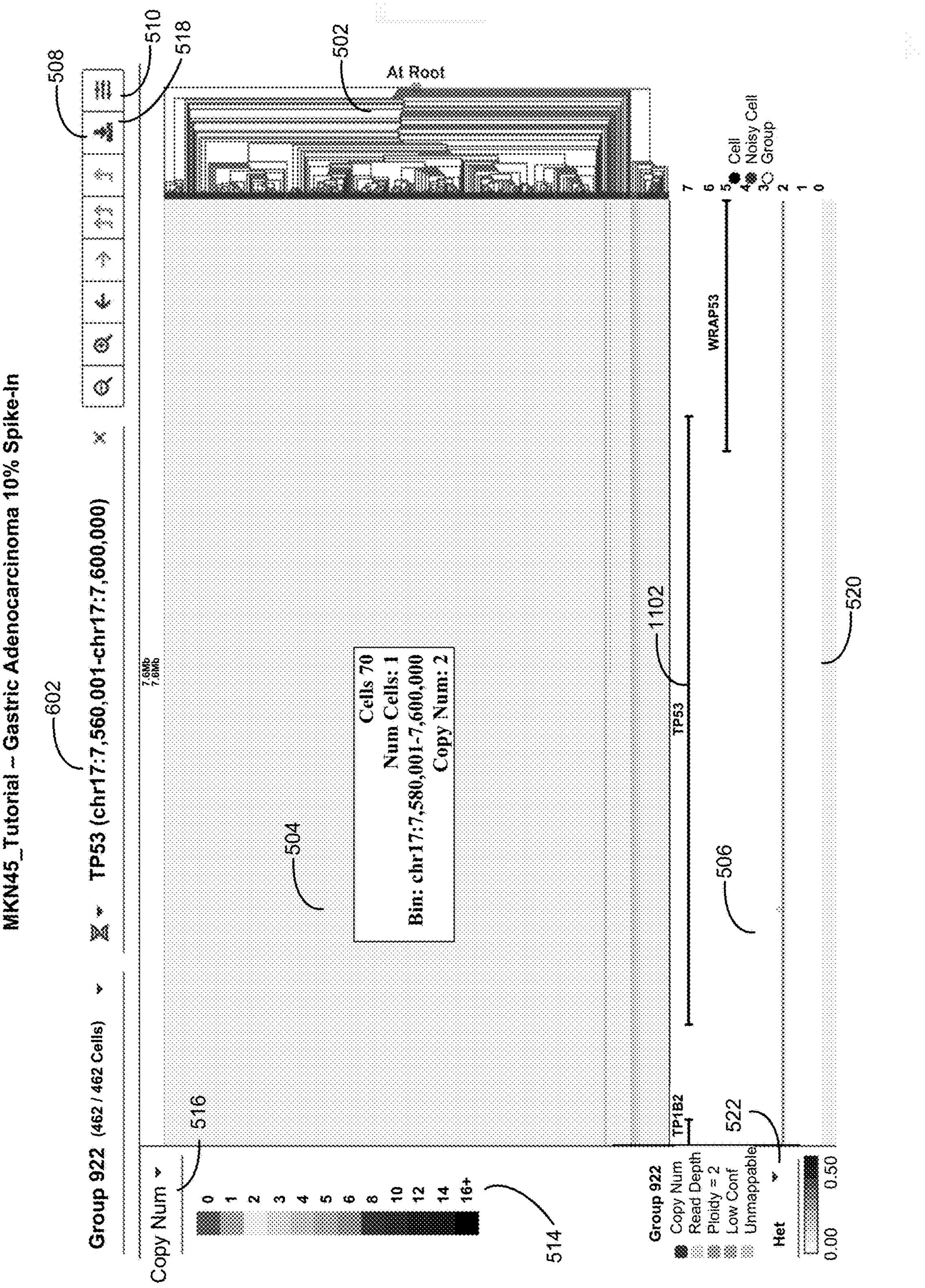
FIG. 11A illustrates how gene annotations are visible when sufficiently zoomed in, or when the user enters a gene in the navigation, where each gene in the annotation is given a constant vertical position and a color, so that they will appear consistent at various zoom levels, in accordance with some embodiments of the present disclosure.
Figure 11B:
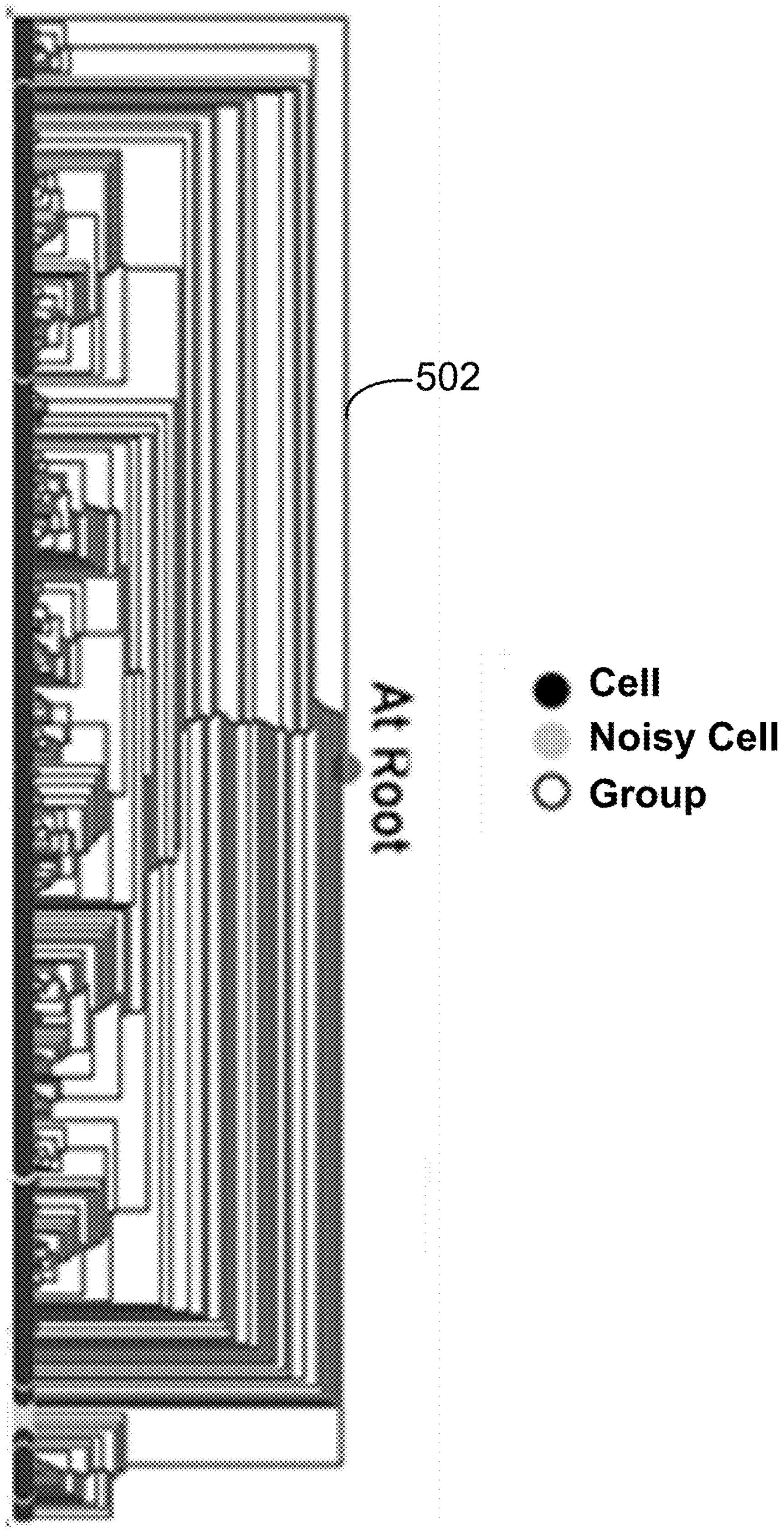
FIG. 11B provides an enlarged view of the tree illustrated in FIG. 11A.

When sufficiently zoomed in, if the pipeline prior to running the analysis module 122 was run on a reference with gene annotations, those genes will be visible when sufficiently zoomed in, or when the user enters a gene in the navigation (see FIG. 11, element 1102, the TP53 gene). Each gene in the annotation is given a constant vertical position and a color, so that they will appear consistent at various zoom levels.

Exporting Data. One can export the contents of the heatmap graph 504 and root panel graph 502, in addition to a screenshot of both, by clicking on the Export (Download) affordance 518 in the map panel 508. In some embodiments, exporting Heatmap Data serializes the visible copy number or heterogeneity values in the heatmap into a comma separated (or other form of delimiter) value (CSV) file. In some embodiments, exporting the selected root data as CSV exports all information about the node in a bin-wise manner.

Example 1—Obtaining Sequence Reads

The analysis module 122 reads and analyzes single cell sequencing datasets 128 in the manner set forth in FIG. 2 and described above. This example provides non-limiting examples of how such single cell sequencing datasets 128 are acquired and how they are barcoded. In some embodiments, such analysis is done by a pipeline that is run before the analysis module 122 loads a dataset 128.

In some embodiments, single cell sequencing is performed as disclosed in U.S. patent application Ser. No.

15/887,947, entitled "Methods and Systems for Droplet-Based Single Cell Barcoding," filed Feb. 2, 2018 (the '947 application), which is hereby incorporated by reference. For instance, the '947 application discloses the production of one or more droplets containing a single cell bead and a single barcode bead. The systems and methods disclosed in the '947 application also allow for the production of one or more droplets containing a single cell bead and more than one barcode bead, one or more droplets containing more than one cell bead and a single barcode bead, or one or more droplets containing more than one cell bead and more than one barcode bead.

Figure 3:
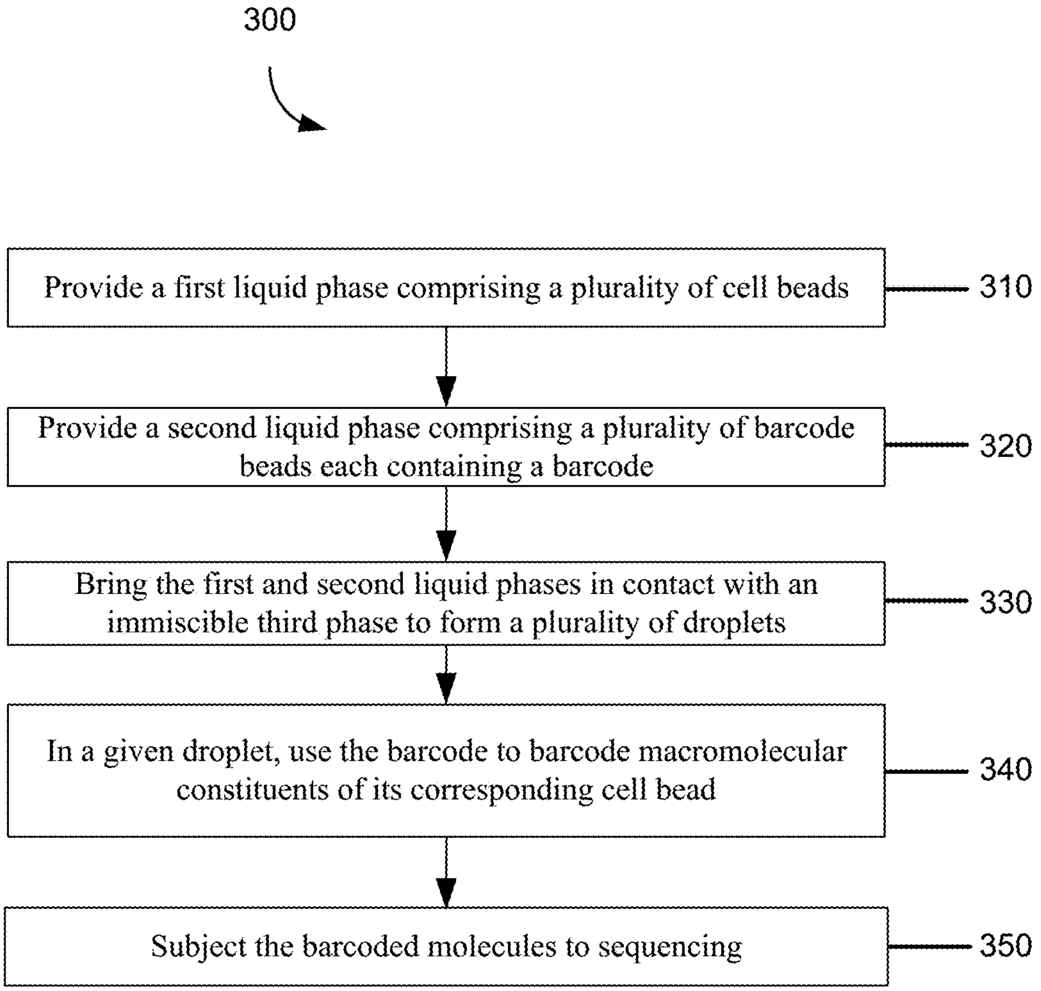
FIG. 3 shows a flowchart for a method of producing droplets containing a cell bead and a barcode bead and generating sequence reads from macromolecular components of the cell bead.

FIG. 3 shows a flowchart for a method of producing droplets containing a cell bead and a barcode bead (e.g., gel bead) comprising a barcode sequence and generating sequence reads from macromolecular components of the cell bead.

In operation 310, a first liquid phase comprising a plurality of cell beads is provided. The first liquid phase may be aqueous. The first liquid phase may comprise a cellular growth medium. The first liquid phase may comprise a minimal growth medium.

In operation 320, a second liquid phase comprising a plurality of barcode beads can be provided. The second liquid phase may be aqueous. The second liquid phase may comprise a cellular growth medium. The second liquid phase may comprise a minimal growth medium. The barcode beads each contain a barcode to barcode one or more macromolecular constituents of the plurality of cell beads. In some cases, the first liquid phase and the second liquid phase are the same phase. In some cases, the first liquid phase and the second liquid phase are mixed to provide a mixed phase.

In operation 330, the first liquid phase and the second liquid phase can be brought together with a third liquid phase that is immiscible with the first and second liquid phase. The third liquid phase may interact with the first and second liquid phases in such a manner as to partition each of the plurality of cell beads and the plurality of barcode beads into a plurality of droplets. The third liquid phase may comprise an oil. The third liquid phase may comprise a fluorinated hydrocarbon. In some cases, a given droplet may include a single cell bead and a single barcode bead. In some cases, at least 80%, at least 90%, at least 95%, at least 99%, at least 99.5%, at least 99.9%, at least 99.95%, or at least 99.99% of the droplets may contain a single cell bead. Moreover, while the first liquid phase and second liquid phase are partitioned into droplets in this example, other types of partitions can be implemented at operation 330, including those described elsewhere within the '947 application, such as a well.

In operation 340, the barcode can be used to barcode one or more macromolecular constituents of a given cell bead in a given droplet. In some cases, the macromolecular constituents of the cell bead are subjected to conditions sufficient for nucleic acid amplification for barcoding. In such cases, a barcode can function as a primer in such amplification. In other cases, ligation can be used for barcoding. In some cases, the macromolecular constituents are released from the cell bead prior to amplification. In some cases, the barcode is used to identify one or more macromolecular constituents of the cell bead. In some cases, a barcoded macromolecule is subjected to nucleic acid sequencing to identify one or more macromolecular components. In some cases, the sequencing is untargeted sequencing. In some cases, the sequencing is targeted sequencing. In some cases, droplets comprise an agent that can release the macromolecular constituents from the cell bead during or prior to barcoding. In some cases, a given barcoded sequencing read can be used to identify the cell (which may have been encapsulated in a cell bead) from which the barcoded sequencing read was generated. Such capability can link particular sequences to particular cells.

In operation 350, the barcoded macromolecules (or derivatives thereof) can be subjected to sequencing to generate reads. The sequencing may be performed within a droplet (or partition). The sequencing may be performed outside of a droplet. For instance, the sequencing may be performed by releasing the barcoded macromolecules from a droplet (e.g., by breaking an emulsion comprising the droplets) and sequencing the barcoded macromolecules using a sequencer, such as an Illumina sequencer or any other sequencer described herein. In some cases, prior to sequencing, the barcoded macromolecules may be further processed. For example, the barcoded macromolecules are subjected to nucleic acid amplification (e.g., PCR) prior to sequencing. In some cases, additional sequences are ligated to barcoded macromolecules. Such further processing may be performed in a droplet or external to the droplet, such as by releasing the barcoded macromolecules from the droplets.

In some cases, the sequencing is nucleic acid sequencing. In some cases, the nucleic acid sequencing is massively parallel sequencing. In some cases, the nucleic acid sequencing is digital polymerase chain reaction (PCR) sequencing. The sequencing may produce target specific reads from macromolecular constituents of interest from a cell bead and non-target specific reads of other macromolecular sequences. The target specific reads may correspond to one or more nucleic acid sequences from a cell bead. In some cases, the non-target specific reads may arise from macromolecules external to the cell bead. For instance, the non-target specific reads may correspond to one or more exogenous nucleic acid sequences. As another example, the non-target specific reads may arise from no-template control effects. The reads may be characterized by a target specific read to non-target specific read ratio. The target specific read to non-target specific read ratio may be greater than 5, greater than 10, greater than 100, greater than 1,000, greater than 10,000, greater than greater than 1,000,000, greater than greater than 10,000,000, greater than 100,000,000, or greater than 1,000,000,000.

Figure 14:
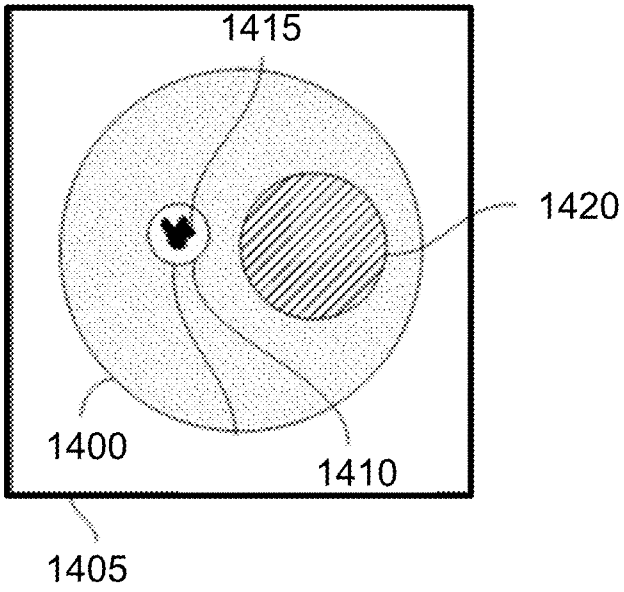
FIG. 14 illustrates a droplet containing a cell bead and a barcode bead produced using the method of FIG. 3.

FIG. 14 shows a droplet containing a cell bead and a barcode bead produced using the method 300 of FIG. 3. A droplet 1400 of aqueous liquid is formed inside a volume 1405 of a liquid that is immiscible with the aqueous liquid. The droplet contains a barcode bead 1420. The droplet also contains a cell bead 1410 containing one or more macromolecular constituents 1415.

Example 2: Correcting for GC Bias

The observed coverage per cell for a fixed bin 126 is influenced by both (i) bin mappability, on the basis that regions with low mappability produce fewer read pairs, (ii) bin GC content, on the basis that a drop in coverage in regions of very low or very high GC content, (iii) scale factor, that is, the number of read pairs generated by a single fragment of DNA in a partition, which is a function of both the underlying library complexity and the sequencing depth, and (iv) bin copy number on the basis that bins that have high copy number have high coverage. These effects can be incorporated into a generative model where DNA in a fixed, unknown copy number state "emits" read pairs that are observed according to a Poisson distribution. The mean of the Poisson distribution is determined by the product of the copy number, the effect of GC content, the mappability, and the scale factor:

$$X_i \sim \text{Poisson}(Sp_iQ(g_i)m_i)$$

where i is an index over all the mappable bins, X is the read coverage, S is the scale factor, p is the copy number, Q(g) is the impact of GC content g, and m the mappability.

Correcting for mappability. In some embodiments the estimation of copy number is restricted to mappable bins 126 of the genome 124 defined as bins with mappability greater than a threshold value as determined by the simulation procedure described earlier. In some embodiments, this threshold value is 90%. In some embodiments, this threshold value is between 80% and 95%. In instances where the threshold value is 90%, such highly mappable bins comprise 85-90% of the human reference genome GRCh37 depending on the sequenced read length and insert size. After restricting to mappable bins the small modulation effect due to varying mappability is ignored in some embodiments.

Correcting for GC bias. To determine the effect of GC content the analysis module 122 aggregates read coverage across a window of consecutive mappable bins 126 to minimize the effects of sampling noise at low depth. In some embodiments, the aggregation window w is approximately the number of bins 126 that would have to be aggregated to reach a mean read count of 200 reads per window. In some embodiments, the aggregation window w is approximately the number of bins 126 that would have to be aggregated to reach a mean read count of 100 reads, 110 reads, 120 reads, 130 reads, 140 reads, 150 reads, 160 reads, 170 reads, 180 reads, 190 reads, 200 reads, 210 reads, 220 reads, 230 reads, 240 reads, 250 reads, 260 reads, 270 reads, 280 reads, 290 reads, or 300 reads per window. In some embodiments, the aggregation window w is approximately the number of bins 126 that would have to be aggregated to reach a mean read count of 200 reads per window.

Figure 12:
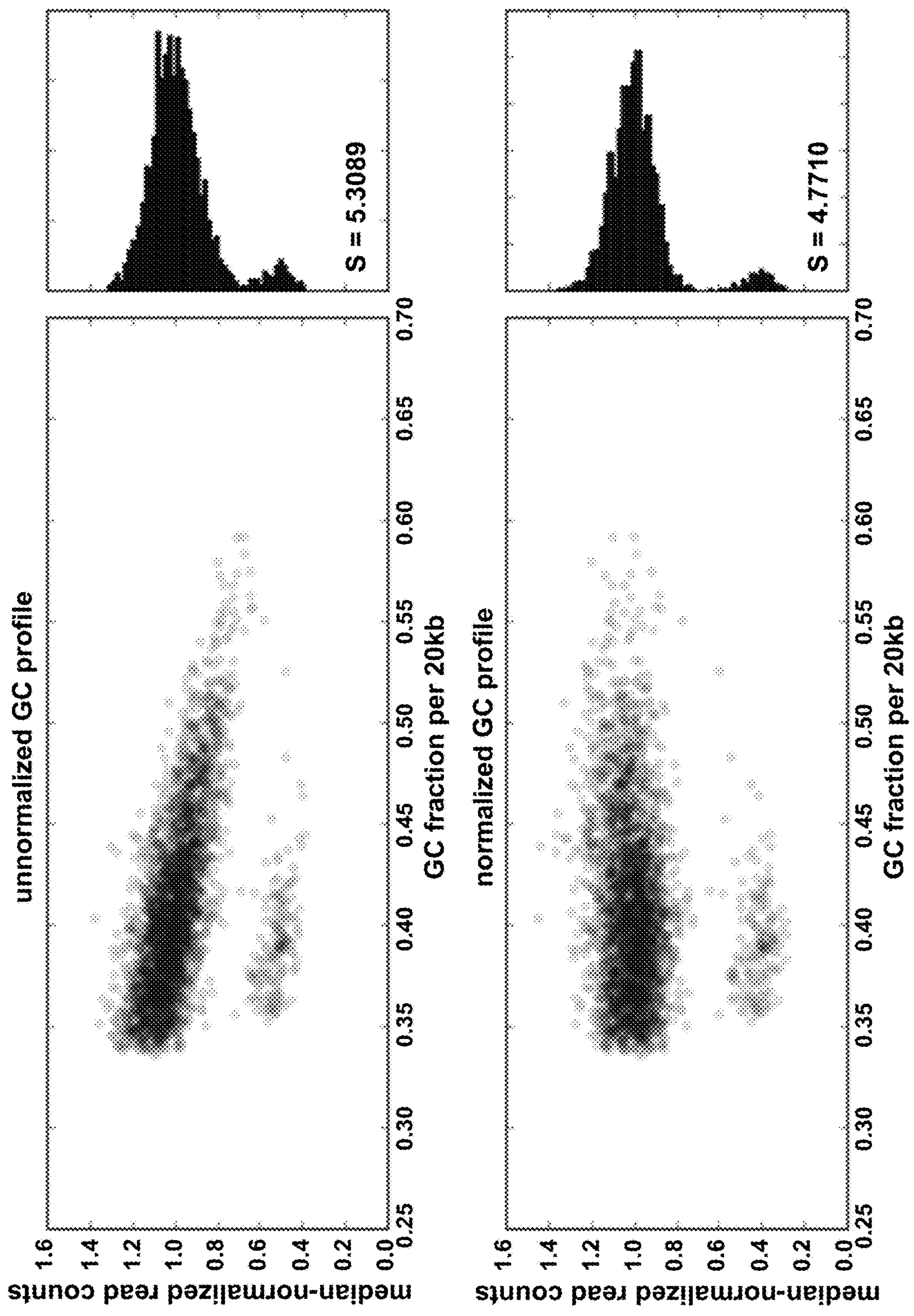
FIG. 12 illustrates the effect of GC content on read coverage, where the top panel shows the read coverage (scaled to a mean of 1.0) plotted against the GC content for a window size w=20 (or 400 kb), and where the top panel shows that distinct bands are due to copy number variation in the cell, the lowest band corresponding to segments of copy number one, the next band to segments of copy number two, etc, whereas the bottom panel shows the results after a GC correction procedure, in accordance with an embodiment of the present disclosure.

The effect of GC content on read coverage is made visually clear in the top panel of FIG. 12, where the read coverage (scaled to a mean of 1.0) is plotted against the GC content for a window size w=20 (or 400 kb). The distinct bands are due to copy number variation in the cell: the lowest band corresponds to segments of copy number one, the next band to segments of copy number two, etc. The bottom panel of FIG. 12 shows the results after the disclosed GC correction procedure. The scaled GC-corrected coverage shows no relationship to the GC content.

In some embodiments the analysis module 122 models the coverage variation as a multiplicative two parameter (l, q) quadratic function Q(g; l, q) of the GC content such that the variation is 1.0 at an arbitrarily chosen value GC=0.45. When l and q are both zero this represents no variation of coverage with GC content. Given values of l and q, the GC-corrected coverage y from the read coverage x is defined as:

$$y_i = \frac{x_i}{Q(g_i; l, q)}$$

where the best fit values of l and q are found by minimizing the entropy of the histogram of y.

Segmenting the genome. In some embodiments breakpoints are identified in the read coverage that separate adjacent regions with distinct copy number by successive application of a log-likelihood ratio test based on the Poisson read-emission model described above. Once all the breakpoints are identified, the regions between two adjacent breakpoints define segments with uniform copy number.

For each mappable bin i in the genome and a half-open interval [l, r) around i the log-likelihood ratio (LLR) is defined as $$LLR(i; l, r) = \sum_{j\in[l,i]} \log\frac{Prob(x_j|\mu_{[l,i)})}{Prob(x_j|\mu_{[l,r)})} + \sum_{j\in[i,r]} \log\frac{Prob(x_j|\mu_{[i,r)})}{Prob(x_j|\mu_{[l,r)})} \text{ where,}$$

$$\mu_{[i,j)} = \frac{\sum_{i\le k<j} X_k}{\sum_{i\le k<j} Q(g_k; l, q)}$$

The LLR helps decide between the hypotheses (1) the interval [l, r) has uniform copy number, and (2) the sub-intervals [l, i) and [i, r) have different copy numbers under the Poisson generative model outlined above. In some embodiments, a significance threshold of 5 and large positive values of LLR greater than 5 favor hypothesis 2 making i a candidate breakpoint while values less than 5 favor hypothesis 1.

Figure 13:
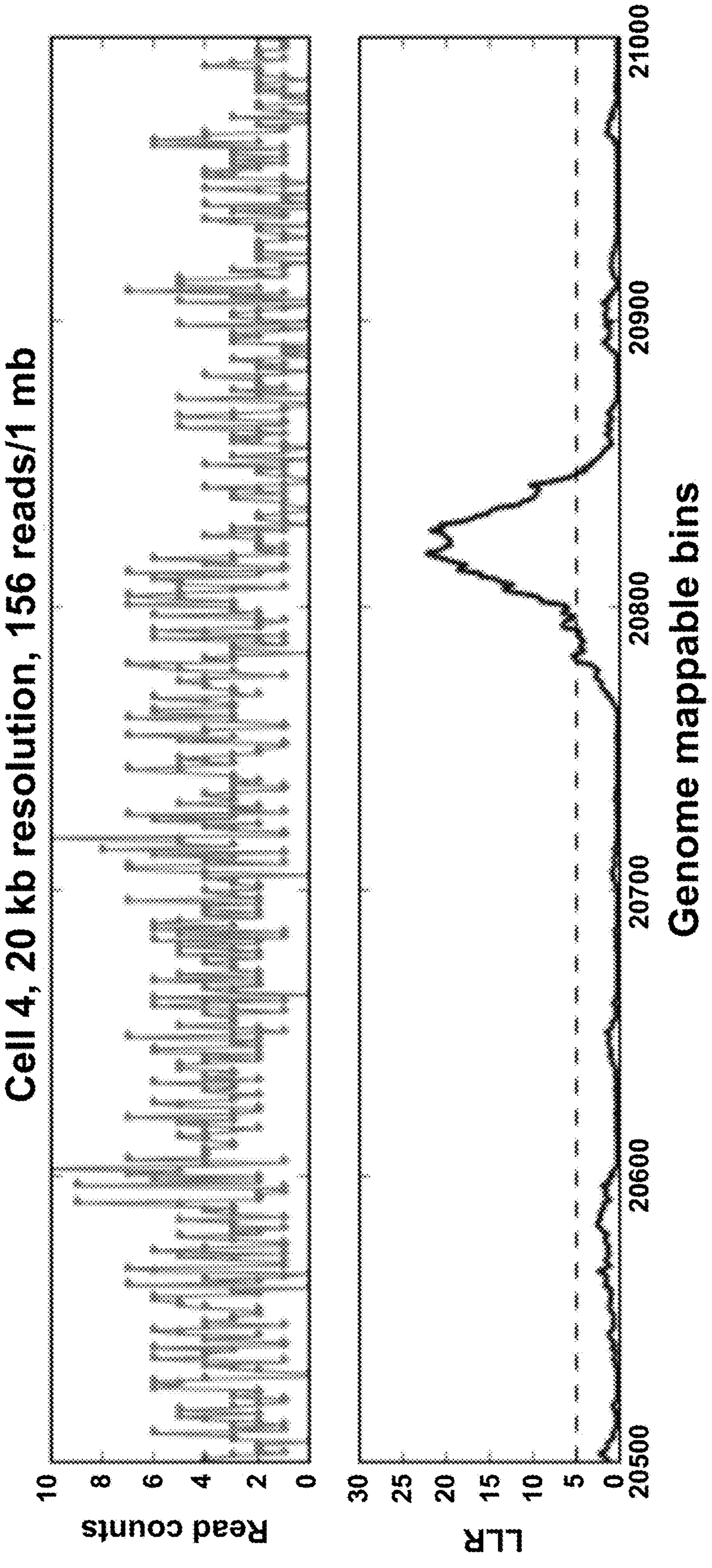
FIG. 13 illustrates the read-pair counts (x) for a single cell having over 500 mappable bins (10 Mb) in the top panel and the calculated log-likelihood ratio for each bin in the bottom panel, in accordance with an embodiment of the present disclosure.

In some embodiments, the LLR at each mappable bin i is calculating using a symmetric interval [i−w, i+w) around i, where w is the aggregation window defined above. FIG. 13 shows the read-pair counts (x) for a single cell having over 500 mappable bins (10 Mb) in the top panel and the calculated log-likelihood ratio for each bin in the bottom panel. The peak above the significance threshold of 5 indicates the presence of one or more breakpoints.

In some embodiments, the following algorithm is used to identify breakpoints. First, all local maxima of the LLR calculated using the aggregation window w above the significance threshold of 5 are selected as an initial candidate breakpoint set B0. For each triple of consecutive breakpoints l, b, r, that value LLR(b; l, r) is calculated and b is discarded if LLR(b; l, r)<5. This gives a smaller set of breakpoints B1. For consecutive breakpoints l, r in B1, the value LLR(i; l, r) is calculated for each bin i in (l, r−1) and if LLR(i; l, r)>5, i is added as a breakpoint. This is repeated until no more breakpoints can be added giving the final set of breakpoints. The genome into a set D of non-overlapping segments [l, r) based on the final breakpoint set where each segment is bounded by consecutive breakpoints l and r.

Scale factor estimation. After segmentation we determine the integer copy number of each segment in D by estimating the scale factor S. In some embodiments, an objective function is defined as the length-weighted sum over all segments [l, r):

$$O(S) = \sum_{[l,r)\in D} (r-l)\sin^2\left(\frac{\pi\mu'_{[l,r)}}{S}\right) \text{ where } \mu'_{[l,r)} = \mu_{[l,r)}w$$

is the segment mean defined as the mean normalized read-pair count for each segment calculated over the aggregation window w. The objective function is minimized when each segment mean is an integer multiple of the scale factor S. The objective function has multiple local minima and each minimum defines a candidate copy number solution:

$$C_i = \text{round}\left(\frac{\mu'_{[l,r)}}{S}\right)$$

where [l, r) is the unique segment that contains the bin i. Candidate solutions that are poor fits to the data or correspond to an average copy number greater than 8 are filtered out in some embodiments. In some embodiments, the following heuristic to determine the best candidate copy number solution (i) if most of the genome has the same copy number, pick the copy number solution where the average ploidy is closest to 2, otherwise (ii) pick the copy number solution that corresponds to the lowest value of the objective function. This procedure results in accurate copy number profiling over regions of the genome with high mappability.

Computing copy number event confidence scores. For every copy number n event in the interval [l, r) the generative Poisson model allows for the calculation of a confidence score using the posterior distribution. For each bin i in the interval [l, r), the approximate posterior is calculated as $$P(n) = \frac{Prob(x_i|n)}{Prob(x_i|n-1) + Prob(x_i|n) + Prob(x_i|n+1)}$$

When Prob(x|0) is encountered using the formula above, which occurs when n=0, 1, Prob(x|0.01) is substituted instead since copy number 0 events do have non-zero read counts due to mis-mapped reads. The Prob(x|n−1) term is dropped in the denominator when n=0. The confidence score for the event is calculated using the bin-wise log-product $$conf = -\frac{100}{(r-l)}\log_{10}\prod_{l\le i<r}(1-P(n))$$

In some embodiments, the score is multiplied by 100 so the confidence score can be truncated to the interval [0, 256) and represented as uint8. When a good fit to the copy number n hypothesis is obtained, P(n) is very close to 1, and the confidence score is large and positive.

Conclusion

All references cited herein are incorporated herein by reference in their entirety and for all purposes to the same extent as if each individual publication or patent or patent application was specifically and individually indicated to be incorporated by reference in its entirety for all purposes.

Plural instances may be provided for components, operations or structures described herein as a single instance. Finally, boundaries between various components, operations, and data stores are somewhat arbitrary, and particular operations are illustrated in the context of specific illustrative configurations. Other allocations of functionality are envisioned and may fall within the scope of the implementation(s). In general, structures and functionality presented as separate components in the example configurations may be implemented as a combined structure or component. Similarly, structures and functionality presented as a single component may be implemented as separate components. These and other variations, modifications, additions, and improvements fall within the scope of the implementation(s).

It will also be understood that, although the terms first, second, etc. may be used herein to describe various elements, these elements should not be limited by these terms. These terms are only used to distinguish one element from another. For example, a first subject could be termed a second subject, and, similarly, a second subject could be termed a first subject, without departing from the scope of the present disclosure. The first subject and the second subject are both subjects, but they are not the same subject.

The terminology used in the present disclosure is for the purpose of describing particular embodiments only and is not intended to be limiting of the invention. As used in the description of the invention and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting (the stated condition or event (" or "in response to detecting (the stated condition or event)," depending on the context.

The foregoing description included example systems, methods, techniques, instruction sequences, and computing machine program products that embody illustrative implementations. For purposes of explanation, numerous specific details were set forth in order to provide an understanding of various implementations of the inventive subject matter. It will be evident, however, to those skilled in the art that implementations of the inventive subject matter may be practiced without these specific details. In general, well-known instruction instances, protocols, structures and techniques have not been shown in detail.

The foregoing description, for purpose of explanation, has been described with reference to specific implementations. However, the illustrative discussions above are not intended to be exhaustive or to limit the implementations to the precise forms disclosed. Many modifications and variations are possible in view of the above teachings. The implementations were chosen and described in order to best explain the principles and their practical applications, to thereby enable others skilled in the art to best utilize the implementations and various implementations with various modifications as are suited to the particular use contemplated.

What is claimed:

1. A visualization system, the visualization system comprising one or more processing cores, a memory, and a display, the memory storing instructions for performing a method for visualizing a pattern using the memory and the display, the method comprising:

obtaining, by the visualization system, a dataset that comprises a block of data, wherein the block of data represents a single-cell characteristic for each cell in a plurality of cells across each bin in a plurality of bins, each respective bin in the plurality of bins maps to a different portion of a reference genome, the plurality of cells is clustered based upon the single-cell characteristic, in the block of data, across each respective bin in the plurality of bins, thereby forming a tree structure that includes a current root node, a plurality of intermediate nodes, and the plurality of cells, and the respective cells in the plurality of cells constitute terminal nodes in the tree structure and each respective intermediate node has a corresponding plurality of daughter nodes, each daughter node being an intermediate node or a cell; and plotting, by the visualization system, the single-cell characteristic for the current root node of the tree on the screen using the dataset, across all or the portion of the plurality of bins.

2. The visualization system of claim 1, wherein the plurality of cells is clustered on a computer system remote from the visualization system prior to obtaining the dataset.

3. The visualization system of claim 1, wherein the single-cell characteristic is copy number, heterogeneity, confidence, or read depth.

4. The visualization system of claim 1, wherein the plurality of cells is obtained from a single human subject.

5. The visualization system of claim 1, wherein the plurality of cells comprises 1000 cells.

6. The visualization system of claim 1, wherein the reference genome is a human reference genome.

7. The visualization system of claim 1, wherein the single-cell characteristic is obtained by single cell sequencing of the plurality of cells.

8. The visualization system of claim 1, wherein the corresponding plurality of daughter nodes for each respective intermediate node consists of two nodes.

9. A non-transitory computer readable storage medium, wherein the non-transitory computer readable storage medium stores instructions, which when executed by a computer system, cause the computer system to perform a method for visualizing a pattern, the method comprising:

obtaining a dataset that comprises a block of data, wherein the block of data represents a single-cell characteristic for each cell in a plurality of cells across each bin in a plurality of bins, each respective bin in the plurality of bins maps to a different portion of a reference genome, the plurality of cells is clustered based upon the single-cell characteristic, in the block of data, across each respective bin in the plurality of bins, thereby forming a tree structure that includes a current root node, a plurality of intermediate nodes, and the plurality of cells, and the respective cells in the plurality of cells constitute terminal nodes in the tree structure and each respective intermediate node has a corresponding plurality of daughter nodes, each daughter node being an intermediate node or a cell; and plotting the single-cell characteristic for the current root node of the tree on the screen using the dataset, across all or the portion of the plurality of bins.

10. A visualization system, the visualization system comprising one or more processing cores, a memory, and a display, the memory storing instructions for performing a method for visualizing a pattern using the memory and the display, the method comprising:

obtaining, by the visualization system, a dataset that comprises a block of data, wherein the block of data represents a single-cell characteristic for each cell in a plurality of cells across each bin in a plurality of bins, each respective bin in the plurality of bins maps to a different portion of a reference genome, the plurality of cells is clustered based upon the single-cell characteristic, in the block of data, across each respective bin in the plurality of bins, thereby forming a tree structure that includes a current root node, a plurality of intermediate nodes, and the plurality of cells, and the respective cells in the plurality of cells constitute terminal nodes in the tree structure and each respective intermediate node has a corresponding plurality of daughter nodes, each daughter node being an intermediate node or a cell;

displaying a subset of the tree on a first portion of the screen, wherein the subset includes the current root node and a plurality of leaves, and wherein each leaf in the plurality of leaves represents an intermediate node in the plurality of intermediate nodes or a cell in the plurality of cells; and displaying a heat map of the single-cell characteristic on the screen, the heat map including a respective segment for each leaf in the plurality of leaves, across all or a portion of the plurality of bins, the respective segment including an average of the single-cell characteristic across all the daughter nodes of a leaf when the leaf represents an intermediate node.

11. The visualization system of claim 10, wherein the plurality of cells is clustered on a computer system remote from the visualization system prior to obtaining the dataset.

12. The visualization system of claim 10, wherein the single-cell characteristic is copy number.

13. The visualization system of claim 10, wherein the single-cell characteristic is heterogeneity.

14. The visualization system of claim 10, wherein the single-cell characteristic is confidence.

15. The visualization system of claim 10, wherein the single-cell characteristic is read depth.

16. The visualization system of claim 10, wherein the plurality of cells is obtained from a single human subject.

17. The visualization system of claim 10, wherein the plurality of cells comprises 1000 cells.

18. The visualization system of claim 10, wherein the reference genome is a human reference genome.

19. The visualization system of claim 10, wherein the single-cell characteristic is obtained by single cell sequencing of the plurality of cells.

20. The visualization system of claim 10, wherein the corresponding plurality of daughter nodes for each respective intermediate node consists of two nodes.

* * * * *